United States Patent
Healy et al.

(10) Patent No.: US 9,925,237 B2
(45) Date of Patent: *Mar. 27, 2018

(54) POLYPEPTIDE-POLYMER CONJUGATES AND METHODS OF USE THEREOF

(71) Applicant: The Regents of the University of California, Oakland, CA (US)

(72) Inventors: Kevin Edward Healy, Moraga, CA (US); Samuel T. Wall, Oslo (NO); Krishanu Saha, Cambridge, MA (US); David V. Schaffer, Danville, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/214,398

(22) Filed: Jul. 19, 2016

(65) Prior Publication Data

US 2017/0112899 A1    Apr. 27, 2017

Related U.S. Application Data

(63) Continuation of application No. 12/933,655, filed as application No. PCT/US2009/038446 on Mar. 26, 2009, now Pat. No. 9,428,561.

(60) Provisional application No. 61/040,556, filed on Mar. 28, 2008.

(51) Int. Cl.
  *A61K 38/00*    (2006.01)
  *C07K 14/47*    (2006.01)
  *A61K 38/17*    (2006.01)
  *A61K 47/48*    (2006.01)

(52) U.S. Cl.
  CPC ...... *A61K 38/1709* (2013.01); *A61K 47/4823* (2013.01); *A61K 47/48176* (2013.01)

(58) Field of Classification Search
  None
  See application file for complete search history.

(56) References Cited

U.S. PATENT DOCUMENTS

| | | |
|---|---|---|
| 2003/0003048 A1 | 1/2003 | Li et al. |
| 2003/0236214 A1 | 12/2003 | Wolff et al. |
| 2004/0038876 A1 | 2/2004 | Pepinsky et al. |
| 2004/0116348 A1 | 6/2004 | Chau et al. |
| 2005/0025752 A1 | 2/2005 | Kutryk et al. |
| 2006/0171920 A1 | 8/2006 | Shechter et al. |
| 2007/0026518 A1 | 2/2007 | Healy et al. |
| 2010/0104585 A1 | 4/2010 | Kiessling et al. |
| 2010/0210509 A1 | 8/2010 | Oh et al. |

FOREIGN PATENT DOCUMENTS

| | | |
|---|---|---|
| WO | WO 2000/045848 | 8/2000 |
| WO | WO 2003/031581 A2 | 4/2003 |
| WO | WO 2005/054860 | 6/2005 |

OTHER PUBLICATIONS

Aoyagi, T., et al., "Peptide Drug Carrier: Studies on Incorporation of Vasopressin into Nano-associates Comprising Poly(ethylene glycol)-poly (L-aspartic acid) Block Copolymer", 1999, Colloids and Surfaces B: Biointerfaces, vol. 16, pp. 237-242.
Arpicco, et al.; "Novel Polyethylene glycol derivatives for preparation of Ribosome-Inactivating Protein Conjugates"; Bioconjugate Chem.; vol. 13, pp. 757-765 (2002).
Cairo, et al. "Control of Multivalent Interactions by Binding Epitope Density", J. Am. Ch Em. Soc., 2002, vol. 124, No. 8, pp. 1615-1619.
Chen, et al. "Mitogenic Activities of Water-Soluble and -Insoluble Insulin Conjugates", Bioconjugate Chem., 1997, vol. 8, pp. 106-110.
Gestwicki, et al., "Influencing Receptor-Ligand Binding Mechanisms with Multivalent Ligand Architecture", J. Am. Chem. Soc., 2002, vol. 124, No. 50.
Glass et al., "Characterization of a hyaluronic acid-Arg-Gly-Asp peptide cell attachment matrix", Biomaterials, 17(11):1101-1108 (1996).
Itoda et al., "Evaluation of the Molecular Recognition of Peptide-Conjugated Polymer", Analytical Sciences, 9:185-187 (2003).
Line et al., "Targeting Tumor Angiogenesis: Comparison of Peptide and Polymer-Peptide Conjugates", J Nuel Med, 46(9):1552-1560 (2005).
Mammen, et al. "Polyvalent Interactions in Biological Systems: Implications for Design and Use of Multivalent Ligands and Inhibitors", Angew. Chem. Int. Ed., 1998, vol. 37, pp. 2754-2794.
Mitra, et al.; "Polymer-Peptide Conjugates for angiogenesis targeted tumor radiotherapy"; Nuclear Medicine and Biology; vol. 33, pp. 43-52 (2006).
Smith, et al.; "Conjugation of arginine-glycine-aspartic acid peptides to thermoreversible N-isopropylacrylamide polymers"; Journal of Polymer Science; vol. 41, No. 24, pp. 3989-4000 (Dec. 15, 2003).

*Primary Examiner* — Jeanette Lieb
(74) *Attorney, Agent, or Firm* — Bozicevic Field & Francis, LLP; Paula A. Borden

(57) ABSTRACT

The present invention provides polypeptide-polymer conjugates. A subject polypeptide-polymer conjugate is useful in a variety of applications, which are also provided.

9 Claims, 7 Drawing Sheets

POLYPEPTIDE-POLYMER CONJUGATES AND METHODS OF USE THEREOF

CROSS-REFERENCE

This application is a continuation of U.S. patent application Ser. No. 12/933,655, filed Nov. 10, 2010, (now U.S. Pat. No. 9,428,561), which is a national stage filing under 35 U.S.C. § 371 of PCT/US2009/038446, filed Mar. 26, 2009, which claims the benefit of U.S. Provisional Patent Application No. 61/040,556, filed Mar. 28, 2008, each of which applications is incorporated herein by reference in its entirety.

STATEMENT REGARDING FEDERALLY SPONSORED RESEARCH

This invention was made with government support under Grant No. AR047304 awarded by the National Institutes of Health. The government has certain rights in the invention.

BACKGROUND

The use of chemical tethers to create solid-phase forms of biologically active agents is a recurring theme across a wide range of medical and biological applications. Chemical tethers can be used to attach bioactive peptides or proteins to surfaces, to impart bioactivity to porous or hydrogel implants, or in drug delivery applications. Solid-phase presentation can alter the way that bioactive molecules function in a biological setting.

SUMMARY OF THE INVENTION

The present invention provides polypeptide-polymer conjugates. A subject polypeptide-polymer conjugate is useful in a variety of applications, which are also provided.

DEFINITIONS

Figure 1:
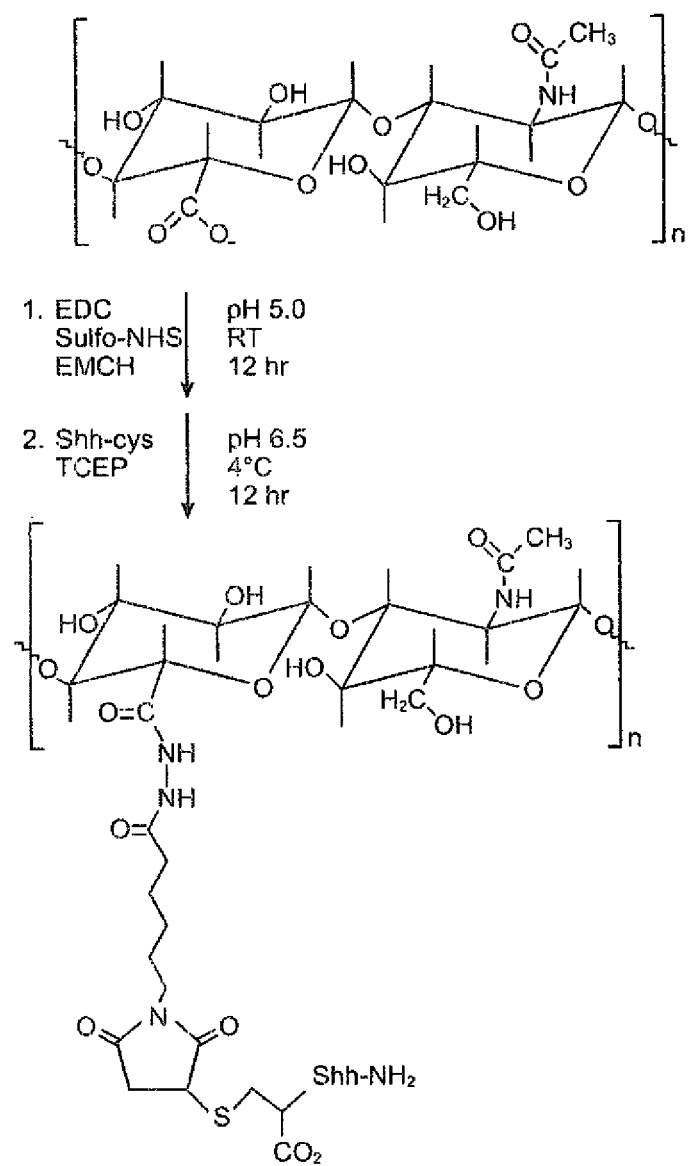
FIG. 1 depicts a bioconjugate scheme to graft a recombinant protein (Shh, sonic hedgehog) to the polymer hyaluronic acid (HyA).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term "polypeptide" includes fusion proteins, including, but not limited to, fusion proteins with a heterologous amino acid sequence, fusions with heterologous and homologous leader sequences, with or without N-terminal methionine residues; immunologically tagged proteins; and the like. The term "polypeptide" includes polypeptides comprising one or more of a fatty acid moiety, a lipid moiety, a sugar moiety, and a carbohydrate moiety. The term "polypeptides" includes post-translationally modified polypeptides.

As used herein, the term "copolymer" describes a polymer which contains more than one type of subunit. The term encompasses polymer which include two, three, four, five, or six types of subunits.

The terms "subject," "individual," "host," and "patient" are used interchangeably herein to a member or members of any mammalian or non-mammalian species. Subjects and patients thus include, without limitation, humans, non-human primates, canines, felines, ungulates (e.g., equine, bovine, swine (e.g., pig)), avians, rodents (e.g., rats, mice), and other subjects. Non-human animal models, particularly mammals, e.g. a non-human primate, a murine (e.g., a mouse, a rat), lagomorpha, etc. may be used for experimental investigations.

"Treating" or "treatment" of a condition or disease includes: (1) preventing at least one symptom of the condition, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient, in combination with another agent, or alone in one or more doses, to effect such treatment for the disease. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a synthetic substrate" includes a plurality of such substrates and reference to "the recombinant polypeptide" includes reference to one or more recombinant polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides polypeptide-polymer conjugates, where such conjugates have controlled attachment stoichiometry. A subject polypeptide-polymer conjugate is useful in a variety of applications, which are also provided.

In some embodiments, a subject polypeptide-polymer conjugate is of the formula:

$$X-(Y)_n-Z,$$

where X is a biologically active polypeptide;

Y is an optional linker moiety, such that n is 0 or an integer from 1 to about 10; and Z is a biocompatible polymer comprising from about 50 to 100,000 subunits.

The biological activity of a polypeptide conjugated to the polymer substrate is enhanced relative to the activity of the polypeptide in soluble form, e.g., compared to the activity of the polypeptide not conjugated to the polymer. In some embodiments, the biological activity of the polypeptide of a subject polypeptide-polymer conjugate is at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, greater than the biological activity of the polypeptide in soluble (unconjugated) form.

In some embodiments, the biological activity of the polypeptide of a subject polypeptide-polymer conjugate is at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, greater than the biological activity of the polypeptide in when conjugated to the polymer at a 1:1 molar ratio.

In some embodiments, the biological activity of the polypeptide of a subject polypeptide-polymer conjugate is at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, greater than the biological activity of the polypeptide when present in admixture with the polymer.

For example, in some embodiments, the $EC_{50}$ of the polypeptide of a subject polypeptide-polymer conjugate is at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, lower than the $EC_{50}$ of the polypeptide in soluble (unconjugated form).

Whether the biological activity of the polypeptide of a subject polypeptide-polymer conjugate is increased relative to the biological activity of the polypeptide in soluble (unconjugated) form is readily determined using an appropriate assay(s) for the biological activity.

The molar ratio of the polypeptide to the polymer can vary from about 5:1 to about 100:1, e.g., from about 5:1 to about 7:1, from about 7:1 to about 10:1, from about 10:1 to about 12:1, from about 12:1 to about 15:1, from about 15:1 to about 20:1, from about 20:1 to about 25:1, from about 25:1 to about 30:1, from about 30:1 to about 35:1, from about 35:1 to about 40:1, from about 40:1 to about 45:1, from about 45:1 to about 50:1, from about 50:1 to about 60:1, from about 60:1 to about 70:1, from about 70:1 to about 80:1, from about 80:1 to about 90:1, or from about 90:1 to about 100:1.

For example, where a subject polypeptide polymer conjugate comprises a polypeptide that induces angiogenesis (e.g., the polypeptide is an angiogenic polypeptide), in some embodiments, the angiogenic polypeptide of a subject polypeptide-polymer conjugate induces at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, more angiogenesis than the angiogenic polypeptide when present in admixture with the polymer, when in soluble (unconjugated) form, or when conjugated to the polymer at a 1:1 molar ratio.

Polymers

Suitable polymers to which a biologically active polypeptide is conjugated include biocompatible polymers comprising from about 50 to about 100,000 subunits, e.g., from about 50 subunits to about 100 subunits, from about 100 subunits to about 500 subunits, from about 500 subunits to about 1,000 subunits, from about 1,000 subunits to about 5,000 subunits, from about 5,000 subunits to about 10,000 subunits, from about 10,000 subunits to about 25,000 subunits, from about 25,000 subunits to about 50,000 subunits, or from about 50,000 subunits to about 100,000 subunits. In some embodiments, the linear polymer comprises more than 100,000 subunits.

The subunits can all be identical, e.g., the polymer is a homopolymer. In other embodiments, more than one species of subunit is present, e.g., the polymer is a heteropolymer or co-polymer. In some embodiments, the polymer is a linear polymer. In other embodiments, the polymer may include one or more branches.

Suitable polymers include natural polymers, semisynthetic polymers, and synthetic polymers.

Suitable natural polymers include hyaluronic acid, collagen, glycosaminoglycans, cellulose, polysaccharides, and the like.

Suitable semisynthetic polymers include, but are not limited to, collagen crosslinked with aldehydes or precursors of the same, dicarboxylic acids or their halogenides, diamines, derivatives of cellulose, hyaluronic acid, chitin, chitosan, gellan gum, xanthan, pectin or pectic acid, polyglycans, polymannan, agar, agarose, natural gums and glycosaminoglycans.

Suitable synthetic polymers include, but are not limited to, polymers or copolymers derived from polydioxane, polyphosphazene, polysulphone resins, poly(acrylic acid), poly(acrylic acid) butyl ester, poly(ethylene glycol), poly(propylene), polyurethane resins, poly(methacrylic acid), poly(methacrylic acid)-methyl ester, poly(methacrylic acid)-n butyl ester, poly(methacrylic acid)-t butyl ester, polytetrafluoroethylene, polyperfluoropropylene, poly N-vinyl carbazole, poly(methyl isopropenyl ketone), poly alphamethyl styrene, polyvinylacetate, poly(oxymethylene), poly(ethylene-co-vinyl acetate), a polyurethane, a poly(vinyl alcohol), and polyethylene terephthalate; ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid) (PGA); poly(D,L-lactic acid) (PLA); copolymers of PGA and PLA; poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; and carboxymethyl cellulose.

The polymer to which the biologically active polypeptide is conjugated can comprise multiple subunits selected from hyaluronic acid, acrylic acid, ethylene glycol, vinyl, propylene, methyl methacrylate, methacrylic acid, acrylamide, hydroxyethyl methacrylate, tetrafluoroethylene, oxymethylene, a sugar (e.g., glucose, mannitol, maltose, arabinose, etc.), taurine, betaine, modified celluloses, hydroxyethyl cellulose, ethyl cellulose, methyl cellulose, hydroxyethyl methyl cellulose, hydroxypropyl methyl cellulose, carboxymethyl cellulose, modified starches, hydrophobically modified starch, hydroxyethyl starch, hydroxypropyl starch, amylose, amylopectin, oxidized starch, an amino acid, and copolymers of any of the foregoing. In some embodiments, the polymer does not include amino acids.

In some embodiments, the polymer is hyaluronic acid or a hyaluronic acid derivative. Hyaluronic acid derivatives include, e.g., a hyaluronic acid ester where part or all of the carboxylic functions are esterified with an alcohol of the aliphatic, aromatic, arylaliphatic, cycloaliphatic or heterocyclic series; a hemiester of succinic acid or a heavy metal salt of the hemiester of succinic acid with hyaluronic acid or with a partial or total ester of hyaluronic acid; sulphated or N-sulphated hyaluronic acid;

Polypeptides

The polypeptide component of a subject polypeptide-polymer conjugate is biologically active, e.g., exhibits one or more biological activities in vivo and/or in vitro. Biological activities include, e.g., antigen binding; activation of a signaling pathway in a eukaryotic cell; induction of cell proliferation; induction of cell differentiation; induction of angiogenesis; induction of apoptosis; induction of angiogenesis; inhibition of angiogenesis; reduction of coagulation; reduction of cell adhesion; enhancement of cell adhesion; control of cell fate; and the like.

The polypeptide component of a subject polypeptide-polymer conjugate can be a naturally-occurring polypeptide, a recombinant polypeptide, or a synthetic polypeptide. The polypeptide can comprise one or more non-amino acid moieties, e.g., a lipid moiety, a sugar moiety, a carbohydrate moiety, etc.

In some embodiments, a single species of polypeptide is attached to a polymer, e.g., a plurality of polypeptides, all having the same amino acid sequence, is attached to a polymer. In other embodiments, two or more species of polypeptides are attached to a polymer, where a first polypeptide has a first amino acid sequence, and a second polypeptide has a second amino acid sequence that is different from the first amino acid sequence (e.g., where the second amino acid sequence has from about 95% to about 99%, from about 90% to about 95%, from about 85% t about 90%, from about 80% to about 85%, from about 75% to about 80%, from about 70% to about 75%, from about 65% to about 70%, or less than 65%, amino acid sequence identity with the first amino acid sequence). For example, the first and the second polypeptides could target different cell surface receptors, e.g., the first polypeptide could provide for cell adhesion through an integrin receptor, and the second polypeptide could provide for activation of a bound cell, e.g., via growth factor receptors, etc. As another example, the first and the second polypeptides could induce cell differentiation, e.g., the first and the second polypeptides could both induce myogenesis, the first and the second polypeptides could both induce cardiomyogenesis, the first and the second polypeptides could both induce neurogenesis, the first and the second polypeptides could both induce differentiation of a progenitor cell into a chondrocyte, or the first and the second polypeptides could both induce hematopoiesis, in a target totipotent, pluripotent, or multipotent progenitor cell.

In some embodiments, the polypeptide component of a subject polypeptide-polymer conjugate is recombinant, e.g., the polypeptide includes one or more amino acids that are not normally in amide bond linkage with the polypeptide. For example, the polypeptide can be engineered to include an amino acid that facilitates linkage to the polymer component of the polypeptide-polymer conjugate. As an example, the polypeptide can be engineered to include a cysteine residue that facilitates linkage to the polymer component of the polypeptide-polymer conjugate.

The size of the polypeptide can range from 2 kDa to about 2000 kDa, e.g., from about 2 kDa to about 5 kDa, from about 5 kDa to about 10 kDa, from about 10 kDa to about 25 kDa, from about 25 kDa to about 50 kDa, from about 50 kDa to about 100 kDa, from about 100 kDa to about 250 kDa, from about 250 kDa to about 500 kDa, from about 500 kDa to about 1000 kDa, from about 1000 kDa to about 2000 kDa.

In some embodiments, the polypeptide component of a subject polypeptide-polymer conjugate comprises a detectable label. Suitable labels include, e.g., radioisotopes (e.g., $^{125}$I; $^{35}$S, and the like); enzymes whose products generate a detectable signal (e.g., luciferase, β-galactosidase, horseradish peroxidase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins (e.g., a green fluorescent protein, a yellow fluorescent protein, a red fluorescent protein, etc.); and the like.

Polypeptides that are of interest for attachment to a polymer, to generate a subject polypeptide-polymer conjugate include, e.g., growth factors, receptors, polypeptide ligands for receptors, enzymes, antibodies, coagulation factors, anti-coagulation factors, angiogenic factors, anti-angiogenic factors, etc. Suitable polypeptides include linear polypeptides and cyclic polypeptides. Suitable polypeptides include naturally occurring polypeptides, synthetic polypeptides, and the like.

Suitable polypeptides include, but are not limited to, an interferon (e.g., IFN-γ, IFN-α, IFN-β, IFN-ω; IFN-τ); an insulin (e.g., Novolin, Humulin, Humalog, Lantus, Ultralente, etc.); an erythropoietin ("EPO"; e.g., Procrit®, Eprex®, or Epogen® (epoetin-α); Aranesp® (darbepoietin-α); NeoRecormon®, Epogin® (epoetin-β); and the like); an antibody (e.g., a monoclonal antibody) (e.g., Rituxan® (rituximab); Remicade® (infliximab); Herceptin® (trastuzumab); Humira™ (adalimumab); Xolair® (omalizumab); Bexxar® (tositumomab); Raptiva™ (efalizumab); Erbitux™ (cetuximab); and the like), including an antigen-binding fragment of a monoclonal antibody; a blood factor (e.g., Activase® (alteplase) tissue plasminogen activator; NovoSeven® (recombinant human factor VIIa); Factor VIIa; Factor VIII (e.g., Kogenate®); Factor IX; β-globin; hemoglobin; and the like); a colony stimulating factor (e.g., Neupogen® (filgrastim; G-CSF); Neulasta (pegfilgrastim); granulocyte colony stimulating factor (G-CSF), granulocyte-monocyte colony stimulating factor, macrophage colony stimulating factor, megakaryocyte colony stimulating factor; and the like); a growth hormone (e.g., a somatotropin, e.g., Genotropin®, Nutropin®, Norditropin®, Saizen®, Serostim®, Humatrope®, etc.; a human growth hormone; and the like); an interleukin (e.g., IL-1; IL-2, including, e.g., Proleukin®; IL-3, IL-4, IL-5, IL-6, IL-7, IL-8, IL-9; etc.); a growth factor (e.g., Regranex® (beclapermin; PDGF); Fiblast® (trafermin; bFGF); Stemgen® (ancestim; stem cell factor); keratinocyte growth factor; an acidic fibroblast growth factor, a stem cell factor, a basic fibroblast growth factor, a hepatocyte growth factor; and the like); a receptor (e.g., a TNF-α-binding soluble receptor such as Enbrel® (etanercept); a VEGF receptor; a interleukin receptor; a γ/δ T cell receptor; and the like); a neurotransmitter receptor (e.g., a nicotinic acetylcholine receptor, a glutamate receptor, a GABA receptor, etc.); an enzyme (e.g., α-glucosidase; Cerazyme® (imiglucarase; β-glucocerebrosidase, Ceredase® (alglucerase); an enzyme activator (e.g., tissue plasminogen activator); a chemokine (e.g., IP-10; Mig; Groα/IL-8, RANTES; MIP-1α; MIP-1β; MCP-1; PF-4; and the like); an angiogenic agent (e.g., vascular endothelial growth factor (VEGF); an anti-angiogenic agent (e.g., a VEGF receptor); a neuroactive peptide such as bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, an insulin-like growth factor, a luteinizing hormone, a macrophage activating factor, tumor necrosis factor, a neutrophil chemotactic factor, a nerve growth factor a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); an ion channel, e.g., cystic fibrosis transmembrane conductance regulator (CFTR); dystrophin; utrophin, a tumor suppressor; lysosomal enzyme acid α-glucosidase (GAA); and the like.

Suitable polypeptides include sonic hedgehog (Shh), bone morphogenic protein-4, interleukin-3 (IL-3), stem cell factor-1 (SCF-1), fms-like tyrosine kinase-3 (Flt3) ligand, leukemia inhibitory factor (LIF), fibroblast growth factor-2 (FGF-2), and epidermal growth factor (EGF). Suitable polypeptides include brain-derived neurotrophic factor (BDNF), nerve growth factor (NGF), neurotrophin-3 (NT-3), neurotrophin-4 (NT-4), neurotrophin-5 (NT-5), basic fibroblast growth factor (bFGF), insulin-like growth factor-1 (IGF-1), glial-derived neurotrophic factor (GDNF), and protease nexin-1. Suitable angiogenic polypeptides include a netrin-1 polypeptide, a vascular endothelial growth factor (VEGF) polypeptide, a platelet-derived growth factor (PDGF) polypeptide, a fibroblast growth factor (FGF) polypeptide, and an angiopoietin polypeptide.

Suitable polypeptides also include clotting factors, e.g., thrombin, etc. Suitable polypeptides also include anti-coagulants. Suitable polypeptides also include cell-binding polypeptides.

Suitable polypeptides also include, e.g., Nestin, Vimentin, Prominin/CD133, Sonic hedgehog and other hedgehog ligands, Wnt ligands, Neurocan/tenascin C, Nun 1, Pax-6, Sox-2, Musashi-1, NG2/CSPG-4, Neuro D3, Neurogenin 1, and active fragments and subsequences of any these polypeptides.

Suitable polypeptides also include, e.g., β tubulin III, MAP2, Neuron specific enolase, NCAM, CD24, HAS, Synapsin I, Synaptophysin, CAMK Iia, Tyrosine hydroxylase, Glutamate transporter, Glutamate receptor, Choline rececptor, nicotinic A2, EphB2, GABA-A receptor, Serotonin (5HT-3) receptor, Choline acetyltransferase, and fragments and subsequences of any of the foregoing.

Suitable polypeptides also include, e.g., a calcium channel; a T-cell antigen receptor; a chemokine receptor; a potassium channel; a neurotransmitter receptor (e.g., a serotonin receptor; a GABA receptor; a glutamate receptor; a nicotinic acetylcholine receptor; etc.); a growth factor receptor (e.g., epidermal growth factor receptor; vascular endothelial growth factor receptor, etc.); a bone morphogenetic protein; a polypeptide that activates a cell signaling pathway; and the like.

The polypeptide component of a subject polypeptide-polymer conjugate is biologically active. Those skilled in the art can readily determine whether a given polypeptide is biologically active, using any of a number of well-known assays designed to test for a particular biological activity. Examples of useful assays for particular biologically active polypeptides include, but are not limited to, GMCSF (Eaves, A. C. and Eaves C. J., Erythropoiesis in culture. In: McCullock E A (edt) Cell culture techniques—Clinics in hematology. W B Saunders, Eastbourne, pp 371-91 (1984); Metcalf, D., International Journal of Cell Cloning 10: 116-25 (1992); Testa, N. G., et al., Assays for hematopoietic growth factors. In: Balkwill F R (edt) Cytokines A practical Approach, pp 229-44; IRL Press Oxford 1991) EPO (bioassay: Kitamura et al., J. Cell. Physiol. 140 p 323 (1989)); Hirudin (platelet aggregation assay: Blood Coagul Fibrinolysis 7(2):259-61 (1996)); IFNα (anti-viral assay: Rubinstein et al., J. Virol. 37(2):755-8 (1981); anti-proliferative assay: Gao Y, et al Mol Cell Biol. 19(11):7305-13 (1999); and bioassay: Czarniecki et al., J. Virol. 49 p 490 (1984)); GCSF (bioassay: Shirafuji et al., Exp. Hematol. 17 p 116 (1989); proliferation of murine NFS-60 cells (Weinstein et al, Proc Natl Acad Sci 83:5010-4 (1986)); insulin ($^3$H-glucose uptake assay: Steppan et al., Nature 409(6818):307-12 (2001)); hGH (Ba/F3-hGHR proliferation assay: J Clin Endocrinol Metab 85(11):4274-9 (2000); International standard for growth hormone: Horm Res, 51 Suppl 1:7-12 (1999)); factor X (factor X activity assay: Van Wijk et al. Thromb Res 22:681-686 (1981)); factor VII (coagulation assay using prothrombin clotting time: Belaaouaj et al., J. Biol. Chem. 275:27123-8(2000); Diaz-Collier et al., Thromb Haemost 71:339-46 (1994)).

Assays for activation of a cell signaling pathway are known in the art. Assays for induction of cell proliferation are known in the art, and include, e.g., $^3$H-thymidine uptake assays, etc. Assays for induction of angiogenesis include, e.g., a chick chorioallantoic membrane (CAM) assay, an in vitro endothelial cell assay, a Matrigel assay, a disc angiogenesis system, and the like. Assays for induction of cell differentiation are known in the art, and include assays to detect gene product(s) associated with a differentiated cell type.

Linkers

As noted above, in some embodiments, a subject polypeptide-polymer conjugate comprises a linker group that links the polypeptide to the polymer. Suitable linkers include peptide linkers, and non-peptide linkers.

A linker peptide may have any of a variety of amino acid sequences. Exemplary peptide linkers are between about 6 and about 40 amino acids in length, or between about 6 and about 25 amino acids in length. Exemplary linkers include poly(glycine) linkers (e.g., (Gly)$_n$, where n is an integer from 2 to about 10); linkers comprising Gly and Ser; and the like.

Conjugation

A variety of conjugation methods and chemistries can be used to conjugate a polypeptide to a polymer. Various zero-length, homo-bifunctional, and hetero-bifunctional crosslinking reagents can be used. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. Homo- and hetero-bifunctional reagents generally contain two identical or two non-identical sites, respectively, which may be reactive with amino, sulfhydryl, guanidino, indole, or nonspecific groups.

In some embodiments, the polymer comprises an amino-reactive group for reacting with a primary amine group on the polypeptide, or on a linker. Suitable amino-reactive groups include, but are not limited to, N-hydroxysuccinimide (NHS) esters, imidoesters, isocyanates, acylhalides, arylazides, p-nitrophenyl esters, aldehydes, and sulfonyl chlorides.

In some embodiments, the polymer comprises a sulfhydryl-reactive group, e.g., for reacting with a cysteine residue in the polypeptide. Suitable sulfhydryl-reactive groups include, but are not limited to, maleimides, alkyl halides, pyridyl disulfides, and thiophthalimides.

In other embodiments, carbodiimides soluble in both water and organic solvent, are used as carboxyl-reactive reagents. These compounds react with free carboxyl groups forming a pseudourea that can then couple to available amines, yielding an amide linkage.

As noted above, in some embodiments, a polypeptide is conjugated to a polymer using a homobifunctional crosslinker.

In some embodiments, the homobifunctional crosslinker is reactive with primary amines. Homobifunctional crosslinkers that are reactive with primary amines include NHS esters, imidoesters, isothiocyanates, isocyanates, acylhalides, arylazides, p-nitrophenyl esters, aldehydes, and sulfonyl chlorides.

Non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy)ethylsulfone (BSOCOES), bis-2-(sulfosuccinimidooxycarbonyloxy)ethylsulfone (sulfo-BSOCOES), ethylene glycolbis(succinimidylsuccinate) (EGS), ethylene glycolbis(sulfosuccinimidylsuccinate) (sulfo-EGS), dithiobis(succinimidylpropionate (DSP), and dithiobis(sulfosuccinimidylpropionate (sulfo-DSP). Non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-,3'-(dimethylenedioxy)dipropionimidate (DDDP), dimethyl-3,3'-(tetramethylenedioxy)dipropionimidate (DTDP), and dimethyl-3,3'-dithiobispropionimidate (DTBP).

Non-limiting examples of homobifunctional isothiocyanates include: p-phenylenediisothiocyanate (DITC), and 4,4'-diisothiocyano-2,2'-disulfonic acid stilbene (DIDS). Non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate. Non-limiting examples of homobifunctional arylhalides include 1,5-difluoro-2,4-dinitrobenzene (DFDNB), and 4,4'-difluoro-3,3'-dinitrophenyl-sulfone. Non-limiting examples of homobifunctional aliphatic aldehyde reagents include glyoxal, malondialdehyde, and glutaraldehyde. Non-limiting examples of homobifunctional acylating reagents include nitrophenyl esters of dicarboxylic acids. Non-limiting examples of homobifunctional aromatic sulfonyl chlorides include phenol-2,4-disulfonyl chloride, and α-naphthol-2,4-disulfonyl chloride. Non-limiting examples of additional amino-reactive homobifunctional reagents include erythritolbiscarbonate, which reacts with amines to give biscarbamates.

In some embodiments, the homobifunctional crosslinker is reactive with free sulfhydryl groups. Homobifunctional crosslinkers reactive with free sulfhydryl groups include, e.g., maleimides, pyridyl disulfides, and alkyl halides.

Non-limiting examples of homobifunctional maleimides include bismaleimidohexane (BMH), N,N'-(1,3-phenylene)bismaleimide, N,N'-(1,2-phenylene)bismaleimide, azophenyldimaleimide, and bis(N-maleimidomethyl)ether. Non-limiting examples of homobifunctional pyridyl disulfides include 1,4-di-3'-(2'-pyridyldithio)propionamidobutane (DPDPB). Non-limiting examples of homobifunctional alkyl halides include 2,2'-dicarboxy-4,4'-diiodoacetamidoazobenzene, α, α'-diiodo-p-xylenesulfonic acid, α, α'-dibromo-p-xylenesulfonic acid, N,N'-bis(b-bromoethyl)benzylamine, N,N'-di(bromoacetyl)phenylhydrazine, and 1,2-di(bromoacetyl)amino-3-phenylpropane.

As noted above, in some embodiments, a polypeptide is conjugated to a polymer using a heterobifunctional reagent. Suitable heterobifunctional reagents include amino-reactive reagents comprising a pyridyl disulfide moiety; amino-reactive reagents comprising a maleimide moiety; amino-reactive reagents comprising an alkyl halide moiety; and amino-reactive reagents comprising an alkyl dihalide moiety.

Non-limiting examples of hetero-bifunctional reagents with a pyridyl disulfide moiety and an amino-reactive NHS ester moiety include N-succinimidyl-3-(2-pyridyldithio)propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio)toluene (SMPT), and sulfosuccinimidyl 6-α-methyl-α-(2-pyridyldithio)toluamidohexanoate (sulfo-LC-SMPT).

Non-limiting examples of heterobifunctional reagents comprising a maleimide moiety and an amino-reactive NHS ester include succinimidyl maleimidylacetate (AMAS), succinimidyl 3-maleimidylpropionate (BMPS), N-.gamma.-maleimidobutyryloxysuccinimide ester (GMBS)N-.gamma.-maleimidobutyryloxysulfosuccinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

Non-limiting examples of heterobifunctional reagents comprising an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino) hexanoylamino)hexanoate (SIAXX), succinimidyl-6-(((4-(iodoacetyl)-amino)methyl)-cyclohexane-1-carbonyl) aminohexanoate (SIACX), and succinimidyl-4 ((iodoacetyl)-amino)methylcyclohexane-1-carboxylate (SIAC).

A non-limiting example of a hetero-bifunctional reagent comprising an amino-reactive NHS ester and an alkyl dihalide moiety is N-hydroxysuccinimidyl 2,3-dibromopropionate (SDBP). A non-limiting example of a hetero-bifunctional reagent comprising an alkyl halide moiety and an amino-reactive p-nitrophenyl ester moiety include p-nitrophenyl iodoacetate (NPIA).

Compositions

The present invention provides compositions, including pharmaceutical compositions, comprising a subject polypeptide-polymer conjugate.

In some embodiments, a subject composition comprises a subject polypeptide-polymer conjugate, wherein the subject polypeptide-polymer conjugate is homogeneous, e.g., all of the polypeptides of the polypeptide-polymer conjugate comprise the same amino acid sequence. For example, in some embodiments, a subject composition comprises a plurality of (e.g., multiple copies of) a subject polypeptide-polymer conjugate, where each polypeptide-polymer conjugate molecule comprises polypeptides that all have the same amino acid sequence.

In other embodiments, a subject composition comprises two or more species of a subject polypeptide-polymer conjugate, e.g., a subject composition comprises a first polypeptide-polymer conjugate, where the first polypeptide-polymer conjugate comprises polypeptides of a first amino acid sequence; and at least a second polypeptide-polymer conjugate, wherein the second polypeptide-polymer conjugate comprises polypeptides of a second amino acid sequence that is different from the first amino acid sequence. In some embodiments, a subject composition comprises a third or additional polypeptide-polymer conjugates. As one non-limiting example, a first polypeptide-polymer conjugate comprises a first polypeptide that provides for binding to an integrin; and a second polypeptide-polymer conjugate that comprises a second polypeptide that activates a cell signaling pathway. Various other combinations of first, second, etc., polypeptides can be used. The ratio of the first polypeptide-polymer conjugate to the second polypeptide-polymer conjugate in a subject composition can be varied, e.g., from about 0:001 to $10^3$ to about $10^3$ to 0.001. Similarly, where a subject composition comprises a first, a second, and a third polypeptide-polymer conjugate, the ratios of the first, second, and third polypeptide-polymer conjugates can be varied.

A subject composition can comprise, in addition to a subject polypeptide-polymer conjugate, one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

The present invention provides compositions comprising a subject polypeptide-polymer conjugate and a pharmaceutically acceptable excipient. Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

As used herein, the terms "pharmaceutically acceptable carrier" and "pharmaceutically acceptable excipient" are used interchangeably, and include any material, which when combined with a subject polypeptide-polymer conjugate does not substantially affect the biological activity of the conjugate, does not induce an immune response in a host, and does not have any substantial adverse physiological effect on the host. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

The pharmaceutical compositions may be formulated for a selected manner of administration, including for example, topical, oral, nasal, intravenous, intracranial, intraperitoneal, intratumoral, peritumoral, subcutaneous, or intramuscular administration. For parenteral administration, such as subcutaneous injection, the carrier can comprise water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for a subject pharmaceutical composition. Suitable biodegradable microspheres are disclosed, for example, in U.S. Pat. Nos. 4,897,268 and 5,075,109.

In some embodiments, a subject pharmaceutical composition is administered parenterally, e.g., intravenously. Thus, the invention provides compositions for parenteral administration which comprise a subject conjugate dissolved or suspended in an acceptable carrier, preferably an aqueous carrier, e.g., water, buffered water, saline, phosphate-buffered saline, and the like. The compositions may contain pharmaceutically acceptable auxiliary substances as required to approximate physiological conditions, such as pH adjusting and buffering agents, tonicity adjusting agents, wetting agents, detergents and the like.

A subject composition can be sterilized by conventional sterilization techniques, or may be sterile filtered. The resulting aqueous solutions can be packaged for use as is, or lyophilized, the lyophilized preparation being combined with a sterile aqueous carrier prior to administration. The pH of the preparations can range from 3 and 11, e.g., from about pH 5 to about pH 9, or from about pH 7 to about pH 8.

Implantable Tissues and Devices

In some embodiments, a subject polypeptide-polymer conjugate is coated onto, layered onto, incorporated into, or forms, an implantable tissue or device, e.g., an artificial tissue; an implant into a tissue; a coating for an implantable device (such as an intravascular stent, an artificial joint, a scaffold, a graft (e.g., an aortic graft), an artificial heart valve, a cerebrospinal fluid shunt, a coronary shunt, a pacemaker electrode, an endocardial lead, etc.); an implantable drug delivery system; and the like. Artificial tissues include, e.g., synthetic heart valves (e.g., a synthetic aortic valve, a synthetic mitral valve, etc.). Stents include, e.g., self-expandable stents, balloon-expandable stents, and stent-grafts. Biomaterials include, e.g., films, gels, sponges, gauzes, nonwoven fabrics, membranes, microspheres, microcapsules, threads, guide channels, and the like.

For example, in some embodiments, a subject polypeptide-polymer conjugate is layered or coated onto or otherwise attached to a matrix, to form a synthetic implantable device. For example, a matrix (also referred to as a "biocompatible substrate") is a material that is suitable for implantation into a subject and onto which a subject polypeptide-polymer conjugate is layered, coated, or otherwise attached. A biocompatible substrate does not cause toxic or injurious effects once implanted in the subject. In one embodiment, the biocompatible substrate is a polymer with a surface that can be shaped into the desired structure that requires repairing or replacing. The biocompatible substrate can also be shaped into a part of a structure that requires repairing or replacing. The biocompatible substrate provides the supportive framework onto which a subject polypeptide-polymer conjugate can be layered, coated, or otherwise attached.

In some embodiments, a matrix or a scaffold comprising attached thereto a subject polypeptide-polymer conjugate further comprises one or more cells and/or one or more cell types bound to the matrix or scaffold comprising the polypeptide-polymer conjugate. Such matrices or scaffolds are useful in the context of tissue engineering, cell culturing, cell transplantation, etc.

In some embodiments, a drug delivery device comprises a subject polypeptide-polymer conjugate. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

In some embodiments, the implantable drug delivery system is programmable to provide for administration of an active agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device is the Synchromed infusion pump (Medtronic).

An implantable drug delivery device can be used to delivery any of a variety of agents, e.g., immune response modifiers, anti-proliferatives, anti-apoptotic agents, anti-mitotic agents, anti-platelet agents, platinum coordination complexes, hormones, anticoagulants, fibrinolytic agents, anti-secretory agents, anti-migratory agents, immunosuppressives, angiogenic agents, angiotensin receptor blockers, nitric oxide donors, antisense oligonucleotides, cell cycle inhibitors, corticosteroids, angiostatic steroids, anti-parasitic drugs, anti-glaucoma drugs, antibiotics, differentiation modulators, antiviral drugs, anticancer drugs, and anti-inflammatory drugs.

Utility

A subject polypeptide-polymer conjugate finds use in various applications, including therapeutic (e.g., drug delivery, implantable devices, tissue engineering, regenerative medicine), diagnostic, drug discovery, and research applications.

Therapeutic Applications

A subject polypeptide-polymer conjugate finds use in various therapeutic applications.

For example, as discussed above, a subject polypeptide-polymer conjugate can be attached to a drug delivery device, where the biologically active polypeptide component of the polypeptide-polymer conjugate confers a functionality, and where the drug delivery device provides a therapeutic agent. For example, the biologically active polypeptide could provide targeting to a particular cell type or tissue type in need of treatment with a therapeutic agent, and the drug delivery device could provide the therapeutic agent in a localized manner.

As another example, the biologically active polypeptide component of a subject polypeptide-polymer conjugate could itself be a therapeutic agent, e.g., by providing for induction of apoptosis in a tumor cell; by inducing coagulation of blood at a treatment site; by inhibiting platelet aggregation; by inducing angiogenesis; by inducing cell differentiation; and the like.

As another example, as discussed above, a subject polypeptide-polymer conjugate can be attached to an implantable medical device, e.g., a stent, a shunt, an artificial valve, a lead, an artificial joint, a graft, an electrode, etc., where the biologically active polypeptide component of the subject polypeptide-polymer conjugate provides a desired activity, e.g., reduction of neointimal hyperplasia restenosis; inhibition of cell proliferation; inhibition of cell adhesion; and the like.

As another example, as discussed above, a subject polypeptide-polymer conjugate can be attached a matrix or a scaffold, where the polypeptide-polymer conjugate provides for cell binding. The matrix or scaffold comprising a subject polypeptide-polymer conjugate with or without cells bound to the polypeptide-polymer conjugate can be introduced into an individual in the context of cell transplantation, tissue engineering, etc.

In some embodiments, a subject polypeptide-polymer conjugate finds use in inducing angiogenesis (e.g., where the polypeptide is one that induces angiogenesis) in an individual in need thereof, e.g., in or near an ischemic tissue.

Research Applications

A subject polypeptide-polymer conjugate finds use in various research applications, e.g., to investigate a cell signaling pathway; and the like. A subject polypeptide-polymer conjugate can be administered to an experimental non-human animal model of a disease, to test the effect of the subject polypeptide-polymer conjugate on a physiological response in the model. A subject polypeptide-polymer conjugate can also be used in drug screening applications.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Synthesis and Characterization of Polypeptide-Polymer Conjugates

A potently active multivalent form of the protein Sonic hedgehog (Shh) was produced by bioconjugation of a modified recombinant form of Shh to the linear polymers polyacrylic acid (pAAc) and hyaluronic acid (HyA) via a two step reaction exploiting carbodiimide and maleimide chemistry. Efficiency of the conjugation was ~75% even at stoichiometric ratios of 30 Shh molecules per linear HyA chain (i.e., 30:1 Shh:HyA). Bioactivity of the conjugates was tested via a cellular assay across a range of stoichiometric ratios of Shh molecules to HyA linear chains, which was varied from 0.6:1 Shh:HyA to 22:1 Shh:HyA. Results indicate that low conjugation ratios decrease Shh bioactivity and high ratios increase this activity beyond the potency of monomeric Shh, with approximately equal activity between monomeric soluble Shh and conjugated Shh at 7:1 Shh:HyA. In addition, high ratio constructs increased angiogenesis determined by the in vivo chick chorioallantoic membrane (CAM) assay. These results are captured by a kinetic model of multiple interactions between the Shh:HyA conjugates and cell surface receptors resulting in higher cell signaling at lower bulk Shh concentrations.

Methods

Recombinant Shh and Bioconjugation Techniques

Using the cDNA of the N-terminal signaling domain of rat Shh previously described(15), base pairs coding for an additional cysteine residue and a 6× His tag were added through PCR onto the C-terminus of the protein to allow for sulfhydryl-based reactions and protein purification, respectively. This tethering site was specifically chosen based on studies demonstrating that this area of the protein is distant from its active site, and inert molecules attached here do not alter activity (16). The produced modified Shh PCR product was inserted into a pBAD-HisA (Invitrogen, Carlsbad, Calif.) plasmid, the resulting plasmid was confirmed by DNA sequencing, and the protein expressed in BL21 (DE3).pLys.E $E.\ coli$ through arabinose induction. After induced protein expression, cells were lysed, and the resulting expressed Shh purified using NiNTA (Qiagen, Valencia, Calif.) binding followed by imidazole elution. The purified protein was dialyzed into pH 7.4 PBS containing 10% glycerol, 2 mM EDTA, and 50 μM $ZnSO_4$.

Purified Shh was conjugated to linear polymers through a 2-step reaction using carbodiimide chemistry at the carboxylate group of the polymer and a maleimide reaction at the protein C-terminal cysteine (FIG. 1). The first step was the addition of [N-ε-maleimidocaproic acid] hydrazide (EMCH, Pierce Biotechnology, Rockford, Ill.) to the linear polymer to allow for the subsequent attachment of the protein. This non-immunogenic hydrazide—maleimide heterobifunctional crosslinker was added to the two linear polymers using the same general procedure, but with slightly different reaction conditions. For pAAc conjugates, 450,000 Da pAAc (Polysciences, Warrington, Pa.) at 2 mg/ml was reacted with 1-ethyl-3-[3-dimethylaminopropyl]carbodiimide hydrochloride (EDC) at 3.9 mg/ml, N-hydroxysulfosuccinimide (sulfo-NHS) at 1.1 mg/ml, and 0.5 mg/ml EMCH at room temperature for 2 hours in pH 6.5 MES buffer as described for the attachment of small peptide sequences (17). For the activation of HyA, a method similar to that previously described for the attachment of hydrazides (9) was used with $10^6$ Da MW HyA. (Genzyme, Cambridge Mass.) This was dissolved and reacted at 3 mg/ml with the same concentrations of EDC, sulfo-NHS, and EMCH used in the pAAc reaction overnight in 0.1 M MES buffer, pH 5.0. After the attachment of the EMCH, the resulting maleimide activated linear polymers were separated from the unconjugated reagents through sequential dilution and centrifugation in 50,000 MW cutoff centrifuge filters (Pall Gellman).

The activated polymers were then reacted with the Shh in varying stoichiometric feed ratios to produce conjugates of varying molecular substitution. This reaction was performed at 4° C. overnight in 0.1 M MES buffer (pH 6.5) containing 50 μM Tris (2-carboxyethyl) phosphine hydrochloride (TCEP, Pierce Biotechnology, Rockford, Ill.) to keep the C-terminus Shh cysteine reduced for duration of the reaction. After the reaction, any remaining maleimide groups on the linear polymer were reduced by the addition of 0.5 mM dithiothreitol and incubation at 4° C. for 1 hr.

All conjugation reactions were assayed by gel electrophoresis, comparing reaction solutions to an equal mass of unreacted Shh to visually inspect protein coupling efficiency. In addition, sets of triplicate Shh:HyA conjugation reactions at 20:1 and 10:1 molar feed ratios of Shh to HyA were dialyzed overnight in 0.1 MES buffer (pH 6.5) using Spectra/Por® Float-A-Lyzer® devices (Spectrum Laboratories, Rancho Dominguez, Calif.) to remove non-conjugated Shh. Protein concentrations in the dialyzed HyA-Shh solutions were then quantified using a microBCA assay (Pierce Biotechnology, Rockford, Ill.).

Bioactivity Assay

In order to test bioactivity, murine embryonic C3H10T1/2 cells (American Type Culture Collection, Manassas Va.) were induced to differentiate into an osteogenic line by exposure to Shh as described elsewhere (18, 19). Briefly, the cells were plated at 5000 cells/well in 96 well plates in normal growth media (αMEM with 10% FBS). After 2 days, the medium was replaced with a low FBS (2%) media and supplemented with the proteins and conjugate reaction solutions. Test conditions included soluble Shh in the range of 1-100 nM, soluble Shh in the same range along with unconjugated HyA at 50 μg/ml, or the Shh:HyA conjugate in quantities such that the concentration of Shh in the media solutions were also 1-100 nM. After incubation for an additional 3 days, the cells were washed and lysed, and the cell lysate was assayed for differentiation by measuring alkaline phosphatase (ALP) activity using the fluorescent probe 9-H-(1,3-dichloro-9,9-dimethylacridin-2-one-7-yl) phosphate (DDAO, Molecular Probes, Eugene Oreg.). Unconjugated polyacrylic acid was shown to inhibit the differentiation of the cells, so bioactivity testing of these conjugates was not performed.

Angiogenesis Assays

Shh is a known angiogenic agent (20). Induction of angiogenesis from soluble Shh and Shh:HyA conjugates was assayed using a CAM window assay. Fertile white leghorn eggs (Charles River, Franklin Conn.) were incubated at 37° C. in a humidified environment until day 8, at which time 2 ml of albumin was removed from the blunt end of the egg, and a small 1 cm×1 cm window was made in the shell on the opposite side. Sterile squares of filter paper loaded with sterile PBS, 0.1 μg of Shh, or 0.1 μg Shh of the 20:1 Shh:HyA feed ratio conjugate were placed directly on the developing CAM. This window was then sealed with parafilm and the eggs returned to the incubator. Angiogenesis around the test materials was microscopically evaluated 3 days later using an Olympus SZX7 stereoscope. High resolution photomicrographs were taken using an attached QImaging Qfire camera. These images were analyzed using ImageJ software to quantify the number of blood vessels per unit length in a square perimeter surrounding the implants at distances of 0.1 and 0.25 cm away from its edge. Linear density measurements for each group were tested for statistical significance using a one-way ANOVA on both the 0.1 and 0.25 cm distance data, followed by pairwise Holm's t-tests of the individual groups.

Molecular Modeling of Shh:HyA Conjugate Cell Signaling

Figure 3:
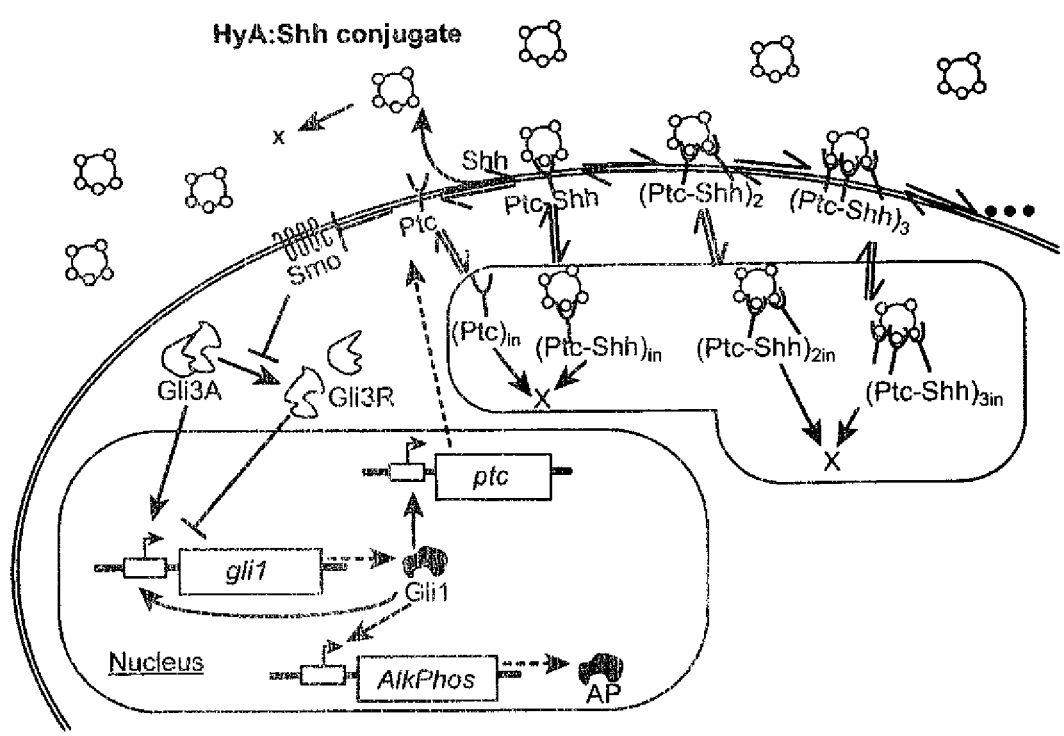
FIG. 3 depicts a schematic of Shh signal transduction pathway and a proposed mechanism for impact of multivalency of Shh on its bioactivity.

Binding and trafficking numerical models that describe expression of Gli transcriptional effectors in response to monomeric Shh (21, 22) and numerical kinetic models describing multivalent ligand-receptor binding (23) (FIG. 3) were built upon to model Shh:HyA conjugate cell signaling. In FIG. 3, the Shh core signaling network and hypothesized reactions involving a multivalent conjugate are shown around a representative cell. Arrows between proteins represent binding or dissociation, arrows from genes to proteins represent expression, and arrows from proteins to genes indicate activation or repression. Smo, Smoothened. At the cellular level, Shh induces cell fate switching by interacting with its transmembrane receptor, Patched (Ptc). In absence of Shh, Ptc represses the signaling activity of the transmembrane protein Smo and therefore acts as a repressor of Shh signaling as described previously (Lai et al., 2004). gli upregulation represents positive feedback, whereas ptc upregulation yields negative feedback. Simulations explore the effect of various mechanisms: binding of HyA:Shh conjugate (avidity); internalization of conjugate-Ptc complexes; and degradation of HyA:Shh.

Nondimensional equations for Shh signaling are shown below:

For Soluble Shh Signal Transduction $$\frac{\partial B}{\partial \tau} = -\alpha_{off}B + \alpha_{on}AD - \beta_{in}B + \gamma_{out}C$$

$$\frac{\partial C}{\partial \tau} = \beta_{in}B - \gamma_{out}C - \Theta_C C$$

$$\frac{\partial D}{\partial \tau} = \alpha_{off}B - \alpha_{on}AD + \alpha_p \text{Promoter} + \beta_p \text{Basal} + \varepsilon_{out}E - \delta_{in}D$$

$$\frac{\partial E}{\partial \tau} = -\varepsilon_{out}E + \delta_{in}D - \Theta_E E$$

$$AP = k_{AP}G_1$$

$$\frac{\partial G_1}{\partial \tau} = \alpha \text{Promoter} + \beta \text{Basal} - G_1$$

$$\frac{\partial G_3}{\partial \tau} = \frac{\gamma}{G_1} - G_3 * \left(\frac{\delta}{Kg3rc + \text{Signal}}\right) - G_3$$

$$\frac{\partial G_{3R}}{\partial \tau} = G_3 * \left(\frac{\delta}{Kg3rc + \text{Signal}}\right) - G_{3R}$$

$$\text{Signal} = \frac{1}{1 + \varsigma D}$$

For Conjugate Signal Transduction

Replace $$\frac{\partial B}{\partial \tau}$$

expressions for cell surface multivalent-receptor complexes of valency i ($Bcom_i$) and maximum valency of $f$:

for $i = 1$ $$\frac{\partial Bcom_1}{\partial \tau} = 2\alpha_{off}Bcom_2 - k_x\alpha_{on}(f-1)Bcom_1D -$$
$$\alpha_{on}AD - \alpha_{off}Bcom_1 + \alpha_{on}AD - \beta_{in}Bcom_1 + \gamma_{out}Ccom_1$$

for $i = [2, f-1]$ $$\frac{\partial Bcom_i}{\partial \tau} = -i\alpha_{off}Bcom_i + k_x\alpha_{on}(f-i+1)Bcom_{i-1}D -$$
$$(f-i)k_x\alpha_{on}Bcom_iD + (i+1)\alpha_{off}Bcom_{i+1} - \beta_{in}Bcom_i + \gamma_{out}Ccom_i$$

for $i = f$ $$\frac{\partial Bcom_f}{\partial \tau} = -f\alpha_{off}Bcom_f + k_x\alpha_{on}Bcom_{f-1}D - B_{in}Bcom_f + \gamma_{out}Ccom_f$$

Replace $$\frac{\partial C}{\partial \tau}$$

expression above with the following expressions for internalized multivalent-receptor complexes of valency i ($Ccom_i$):

for $i = [1, f]$ $$\frac{\partial Ccom_i}{\partial \tau} = \beta_{in}Bcom_i - \gamma_{out}Ccom_i - \Theta_C Ccom_i$$

Replace $$\frac{\partial D}{\partial \tau}$$

expression above with the following:

$$\frac{\partial D}{\partial \tau} = \alpha_{off}\sum_1^f (i)Bcom_i - k_x\alpha_{on}\sum_1^{f-1}(f-i)Bcom_i -$$
$$\alpha_{on}AD + \alpha_p\text{Promoter} + \beta_p\text{Basal} + \varepsilon_{out}E - \delta_{in}D$$

Initial conditions, parameters, and variable descriptions are listed with their literature sources in Table 1. "Promoter" and "Basal" terms have been previously defined (Lai, Robertson et al. 2004). See Saha and Schaffer Development, 2006 for sensitivity analysis of parameters in the soluble Shh network.

Figure 4:
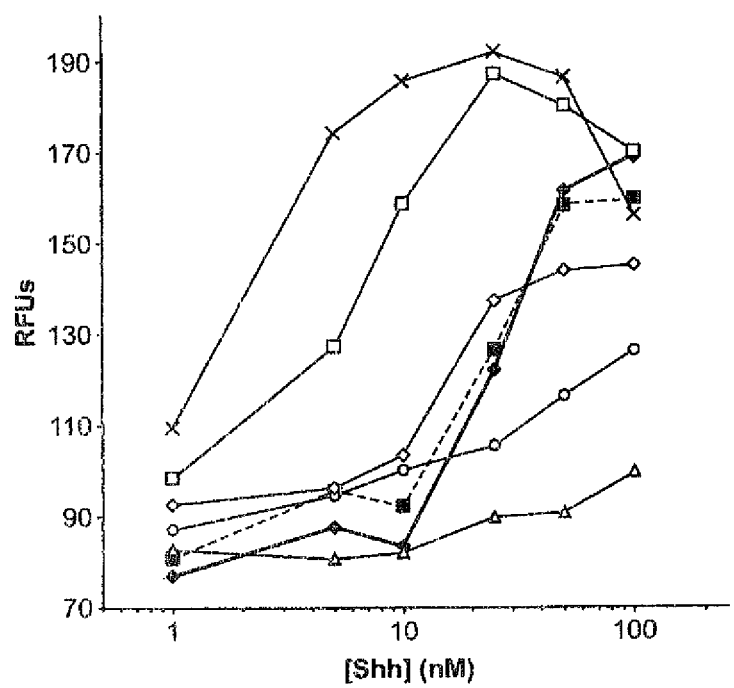
FIG. 4 depicts C3H10T1/2 bioactivity results against soluble Shh (♦, heavy line), soluble Shh with soluble HyA (■, dashed lines), and the Shh-HyA conjugates in stoichiometric ratios of 0.6:1 (Δ), 3.5:1 (○), 7:1 (◇), 14:1 (□), and 22:1 (x).

To develop the simplest model for the C3H10T1/2 bioactivity data in FIG. 4, the following assumptions were invoked: Patched (Ptc) repression of Smoothened is not affected by the Ptc receptor aggregation; ligand-induced internalization rate is the same for all valencies; alkaline phosphatase activity is linearly proportional to Gli1 levels in a cell; and differentiation of a C3H10T1/2 cell does not change its responsiveness to Shh. Initial binding of the HyA:Shh conjugate was assumed to follow monomeric Shh-Ptc binding rates, but all other additional binding of Shh moieties from the conjugate to other Ptc receptors were assumed to occur at a higher rate. This assumption has been called the equivalent site hypothesis to take into account the acceleration of binding after initial binding of a multivalent conjugate (24).

Figure 7:
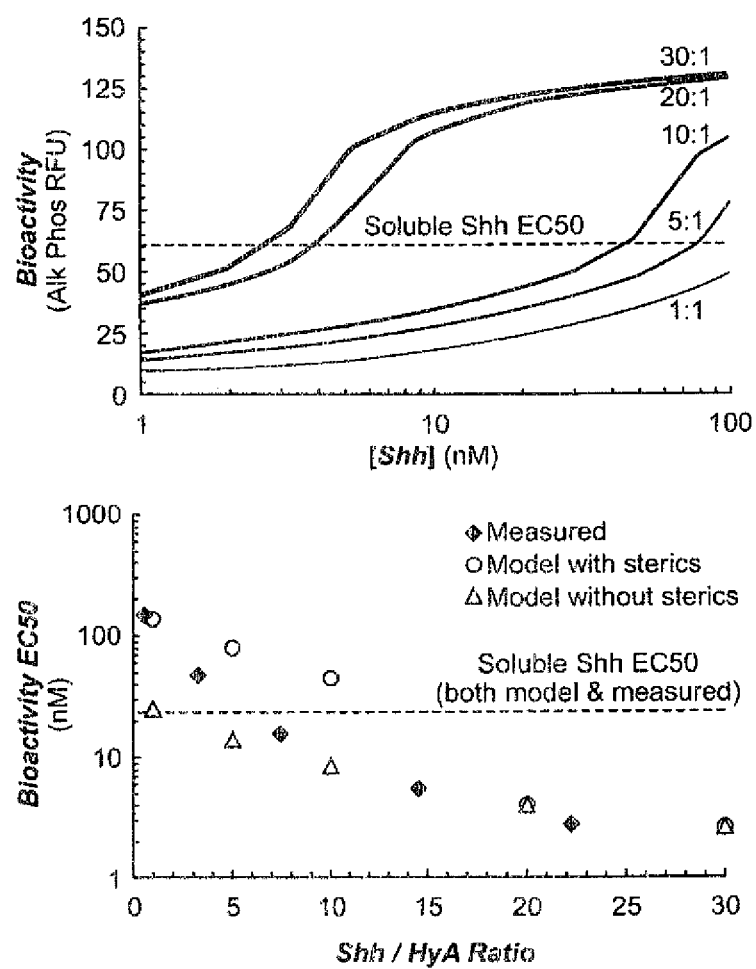
FIG. 7 depicts numerical model results of Shh-HyA conjugate bioactivity in C3H10T1/2 cells. The upper panel presents activity as a function of Shh concentration for the stoichiometric ratios 1:1-30:1 for a model incorporating steric interaction. The lower panel presents a plot of $EC_{50}$ versus substitution level for two types of models versus experimental results.

Model parameters were taken from literature(21, 22); however, a number of parameters were estimated directly from the bioactivity data in FIG. 4. First, the monomeric Shh-Ptc binding constant $k_{on}/k_{off}$ and the alkaline phosphatase activity:Gli1 expression ratio were estimated from the soluble Shh bioactivity curve. In addition, the multimeric Shh-Ptc binding constant was directly estimated from the 22:1 conjugate curve (See Table 1). Parameters were taken either from Shh literature or from similar ligand-receptor systems. All cellular rate constants are averaged within the volume or surface of the cell, since these constants are not known to vary spatially within a cell. The initial conditions for the simulation results shown in FIG. 7 are listed with each variable. A convenient way to understand the relative importance of every term in the differential equations is to compare nondimensional concentrations and parameters in Table 1.

TABLE 1

Parameters definitions and value ranges.

| Dimensional Parameter | Description | Value/Range | Source | Non-dimensional Parameter | Value/Range | Nondimensionalization |
|---|---|---|---|---|---|---|
| | | | Core Signaling Pathway | | | |
| [Shh] | Extracellular Shh concentration | Initial Condition = 0 | variable | A | Initial Condition = 0 | (mol membrane Shh)/(L of extracellular liquid volume)/(Kgli3)/(vff) |
| [PtcShh$_{in}$] | Extracellular PtcShh concentration | Initial Condition = 0 | variable | B | Initial Condition = 0 | (mol membrane Ptc-Shh complex)/(L of extracellular liquid volume)/(Kgli3)/(vff) |
| [PtcShh$_{out}$] | Intracellular PtcShh concentration | Initial Condition = 0 | variable | C | Initial Condition = 0 | (mol intracellular Ptc-Shh complex)/(L of intracellular liquid volume)/(Kgli3) |
| [Ptc$_{out}$] | Extracellular Ptc concentration | Initial Condition = 2.0 nM | variable | D | Initial Condition = 0.605 | (mol membrane free Ptc)/(L of extracellular liquid volume)/(Kgli3)/(vff) |
| [Ptc$_{in}$] | Intracellular Ptc concentration | Initial Condition = 0.33 nM | variable | E | Initial Condition = 0.402 | (mol intracellular Ptc-Shh complex)/(L of intracellular liquid volume)/(Kgli3) |
| [Gli1] | Intracellular Gli1 concentration | Initial Condition = 1.63 nM | variable | $G_1$ | Initial Condition = 1.97 | (mol intracellular Gli1)/(L of intracellular liquid volume)/(Kgli3) |
| [Gli3] | Intracellular Gli3 concentration | Initial Condition = 5.81 nM | variable | $G_3$ | Initial Condition = 7.00 | (mol intracellular Gli3)/(L of intracellular liquid volume)/(Kgli3) |
| [Gli3R] | Intracellular Gli3 Repressor concentration | Initial Condition = 61.2 nM | variable | $G_{3R}$ | Initial Condition = 18.44 | (mol intracellular Gli3 Repressor)/(L of intracellular liquid volume)/(Kgli3) |
| vf | Void fraction of tissue | 0.2 | (Lauffenburger and Linderman 1993) | | | |
| vff | intracellular volume/extracellular volume | 4 | (1 − vf)/vf | | | |
| $k_{deg}$ | Degradation rate constant for Gli1 | 0.009 min$^{-1}$ | (Chen, Kessler et al. 1999) | | | |
| $K_{Gli3}$ | Dissociation constant for Gli3 binding to Gli1 DNA binding site | 8.3 × 10$^{-10}$M | (Lai, Robertson et al. 2004) | | | |
| $K_{shh}$ | Dissociation constant for Shh-Ptc binding | 8.5 × 10$^{-10}$M for model without sterics; 4.5 × 10$^{-9}$M for model with sterics | (Fuse, Maiti et al. 1999; Taipale, Cooper et al. 2002) | | | |
| $k_{off}$ | Dissociation of Shh from Ptc | 0.10 min$^{-1}$ | 0.3 min$^{-1}$ for EGF (Lauffenburger and Linderman 1993) | $\alpha_{off}$ | 11 | $k_{off}/k_{deg}$ |

TABLE 1-continued

Parameters definitions and value ranges.

| Dimensional Parameter | Description | Value/Range | Source | Non-dimensional Parameter | Value/Range | Nondimensionalization |
|---|---|---|---|---|---|---|
| $k_{on}$ | Association of Shh with Ptc | $120,000,000 M^{-1} min^{-1}$ for model without sterics; $22,666,667 M^{-1} min^{-1}$ for model with sterics | $k_{off}/K_{shh}$ | $\alpha_{on}$ | 44.44 | $k_{on} * (K_{Gli3} * vff)/k_{deg}$ |
| $k_{Cdeg}$ | Degradation rate constant for intracellular Shh-Ptc complex | $0.00198 \ min^{-1}$ | $0.0022 \ min^{-1}$ for EGF (Lauffenburger and Linderman 1993) | $\Theta_C$ | 0.220 | $k_{Cdeg}/k_{deg}$ |
| $k_{Pin}$ | Import to endosome of surface free receptors | $0.03 \ min^{-1}$ | for EGFR (Lauffenburger and Linderman 1993) | $\delta_{in}$ | 3.33 | $k_{Pin}/k_{deg}$ |
| $k_{Pout}$ | Recycle to surface of endosomal free receptors | $0.00036 \ min^{-1}$ | $0.058 \ min^{-1}$ (Lauffenburger and Linderman 1993); $0.003 \ min^{-1}$ for Dpp (Lander, Nie et al. 2002) | $\epsilon_{out}$ | 0.0403 | $k_{Pout}/k_{deg}$ |
| $k_{Cin}$ | Import to endosome of surface Shh-bound complexes | $0.2 \ min^{-1}$ | $0.03\text{-}0.3 \ min^{-1}$ for EGF (Lauffenburger and Linderman 1993) | $\beta_{in}$ | 33.3 | $k_{Cin}/k_{deg}$ |
| $k_{Cout}$ | Export to surface of intracellular Shh-bound complexes | $0.00181 \ min^{-1}$ | $0.00402 \ min^{-1}$ for Dpp (Lander, Nie et al. 2002) | $\gamma_{out}$ | 0.20 | $k_{Cout}/k_{deg}$ |
| $k_{Gmax}$ | Maximum rate of Gli synthesis | $1.99 \times 10^{-10} M \ min^{-1}$ | $2.4 \times 10^{-10} M \ min^{-1}$ (Lai, Robertson et al. 2004) | $\alpha$ | 30.4 | $k_{Gmax}/(K_{Gli3} * k_{deg})$ |
| $k_{Gbas}$ | Basal rate of Gli synthesis | $1.53 \times 10^{-12} M \ min^{-1}$ | $k_{Gmax}/130$ | $\beta$ | 0.233 | $k_{Gbas}/(K_{Gli3} * k_{deg})$ |
| $r_{g3b}$ | Basal rate of Gli3 synthesis | $3.1 \times 10^{-19} M^2 \ min^{-1}$ | $1.6 \times 10^{-19} M^2 \ min^{-1}$ (Lai, Robertson et al. 2004) | $\gamma$ | 50.0 | $r_{g3b}/(K_{Gli3} * K_{Gli3} * k_{deg})$ |
| $k_{Pdeg}$ | Degradation rate constant for Ptc | $0.09 \ min^{-1}$ | $0.045\text{-}0.071 \ min^{-1}$ (French and Lauffenburger 1996); $0.006 \ min^{-1}$ (Lander, Nie et al. 2002) | $\Theta_E$ | 10.0 | $k_{Pdeg}/k_{deg}$ |
| $K_{ptc}$ | Half-maximal conc for Ptc which inhibits Smo signaling | $3.32 \times 10^{-11} M$ | $8.3 \times 10^{-11} M$ (Taipale, Cooper et al. 2002) | $\zeta$ | 2.50 | $K_{Gli3}/K_{ptc}$ |
| $k_{g3r}$ | Rate constant for the conversion of Gli3 to Gli3R | $0.0117 \ min^{-1}$ | $0.0117 \ min^{-1}$ (Lai, Robertson et al. 2004) | $\delta$ | 1.30 | $k_{g3r}/k_{deg}$ |

TABLE 1-continued

Parameters definitions and value ranges.

| Dimensional Parameter | Description | Value/Range | Source | Non-dimensional Parameter | Value/Range | Nondimensionalization |
|---|---|---|---|---|---|---|
| $k_{Pmax}$ | Maximum rate of Ptc synthesis | $1.50 \times 10^{-10}$ M min$^{-1}$ | $7.5 \times 10^{-10}$ M min$^{-1}$ (Lai, Robertson et al. 2004); Set from soluble curve in FIG. 3 | $\alpha_P$ | 5.01 | $k_{Pmax}/(K_{Gli3} * vff * k_{deg})$ |
| $k_{Pbas}$ | Basal rate of Ptc synthesis | $1.15 \times 10^{-12}$ M min$^{-1}$ | $k_{Pmax}/130$ | $\beta_P$ | 0.0385 | $k_{Pbas}/(K_{Gli3} * vff * k_{deg})$ |
| $K_{g3rc}$ | Sensitivity constant of the conversion to signal strength | 0.12 | 0.1 (Lai, Robertson et al. 2004) | | | |
| bc | Binding cooperativity | 1 | (Keller 1995) | | | |
| tc | Transcriptional efficiency | 0.5 | (Keller 1995) | | | |
| r | Transcriptional repression | 0.2 | (Lai, Robertson et al. 2004) | | | |
| Afr | Affinity ratio between Gli1 and Gli3 for DNA binding site | 0.5 | | | | |
| $k_{AP}$ | Ratio of Gli1 protein to RFU units of Alkaline Phosphatase activity | 9.3 | Set from soluble curve in FIG. 3 | | | |
| Multivalent Conjugate Reactions | | | | | | |
| $[PtcShh_{i,in}]$ | Extracellular PtcShh concentration of valency i | Initial Condition = 0 | variable | $Bcom_i$ | Initial Condition = 0 | (mol membranic Ptc-Shh$_i$ complex)/(L of extracellular liquid volume)/(Kgli3)/(vff) |
| $[PtcShh_{i,out}]$ | Intracellular PtcShh concentration of valency i | Initial Condition = 0 | variable | $Ccom_i$ | Initial Condition = 0 | (mol intracellular Ptc-Shh$_i$ complex)/(L of intracellular liquid volume)/(Kgli3) |
| i | Valency index to maximum valency of f | | 1, 2, 3, . . . f | | | |
| $k_x$ | Factor by which binding of second and other Shh moeties on conjugate bind to Ptc | 12 | Set from 22:1 curve in FIG. 3 | | | |

An alternative model that incorporates steric hindrance of HyA chains as a simple reduction in conjugate binding affinity to Ptc was also formulated. For the alternative model incorporating sterics, termed the "model with sterics," the multimeric Shh-Ptc binding constant $k_{on}$ for 0.6:1, 3.5:1, and 7:1 conjugation feed ratios was reduced 5.5 fold to match the experimental data from the 0.6:1 curve in FIG. 4. Below is the BERKELEY MADONNA code for the simulations for a multivalent conjugate, where f=5 (5:1 Shh:HyA conjugate). The code below is termed "model without sterics" in the main text. As mentioned in the Methods section, for the "model with sterics," only one parameter change was made: the multimeric Shh-Ptc binding constant $k_{on}$ was reduced 5.5 fold to match the experimental data from the 0.6:1 curve in FIG. 4.

```
METHOD RK4
STARTTIME = 0
STOPTIME=500
DT = 0.0000002
Shh=S*Kshh
; ------------------------------------------------------------------------------------------
;Define Promoter and Basal variable from Lai et. al. Biophys J. 2004
; K1 = equilibrium dissociation binding constant of Gli1
; K2 = equilibrium dissociation binding constant of Gli3
; afr = affinity ratio = K2/K1
; bc = binding cooperativity
; tc = transcriptional cooperativity
; r = repression ratio
; ------------------------------------------------------------------------------------------
; Gli Core Promoter and Basal expressions from Lai et. al. Biophys J. 2004
Promoter=((afr*G1 + G3)*(afr^2*bc^2*G1^2 + 3*tc^2 + 3*bc*tc*(G3 + 2*G3R*r*tc) +
afr*bc*G1*(2*bc*G3 + 3*tc + 3*bc*G3R*r*tc) + bc^2*(G3^2 + 3*G3*G3R*r*tc +
3*G3R^2*r^2*tc^2)))/(1 + afr^3*bc^2*G1^3 + bc^2*G3^3 + 3*G3R + 3*bc*G3R^2 + bc^2*G3R^3 +
3*bc*G3^2*(1 + bc*G3R) + 3*G3*(1 + bc*G3R)^2 + 3*afr^2*bc*G1^2*(1 + bc*(G3 + G3R)) +
3*afr*G1*(1 + bc*(G3 + G3R))^2)
Basal=((1 + afr^3*bc^2*G1^3 + bc^2*G3^3 + 3*G3R*r + 3*bc*G3R^2*r^2 + bc^2*G3R^3*r^3 +
3*bc*G3^2*(1 + bc*G3R*r) + 3*G3*(1 + bc*G3R*r)^2 + 3*afr^2*bc*G1^2*(1 + bc*(G3 + G3R*r)) +
3*afr*G1*(1 + bc*(G3 + G3R*r))^2))/(1 + afr^3*bc^2*G1^3 + bc^2*G3^3 + 3*G3R + 3*bc*G3R^2 +
bc^2*G3R^3 + 3*bc*G3^2*(1 + bc*G3R) + 3*G3*(1 + bc*G3R)^2 + 3*afr^2*bc*G1^2*(1 + bc*(G3
+ G3R)) + 3*afr*G1*(1 + bc*(G3 + G3R))^2)
; ------------------------------------------------------------------------------------------
;Define dimensional constants for Shh binding and transport equations
; ------------------------------------------------------------------------------------------
koff=0.1 ; dissociation of Shh from Ptc (min-1)
kdegc=0.00198 ; Degradation rate constant for Shh-Ptc complex (min-1)
kp=0.03 ; Lauffenburger for EGF keR=3e-2 min-1 (p95)
kq=0.00036 ; Lauffenburger for EGF krec=5.8e-2 min-1 (p95)
kin=0.021 ; Lauffenburger for EGF keC=0.03-0.3 min-1 (p95)
kout=0.00181 ; Export to surface of intracellular Shh-Ptc complex (min-1)
kg=0.09 ; Degradation rate constant for Ptc (.045-0.071 min-1)
kon=koff/Kshh ; Association of Shh with Ptc
vf=0.2 ; void fraction of tissue
vff=(1-vf)/vf ; void fraction factor = intracellular volume/extracellular volume
Do=2.0e-9 ; initial free Ptc concentration for slider in (mol membranic free Ptc) / (L of extracellular
liquid volume)
Eo=0.33e-9 ; initial internal Ptc concentration for slider in (mol internal Ptc) / (L of intracellular liquid
volume)
; ------------------------------------------------------------------------------------------
;Define nondimensional constants
; time in units of 1/kdeg, Degradation rate constant for Gli 1 (.009 min-1)
; ------------------------------------------------------------------------------------------
theta_e=kg/kdeg
alph_off=koff/kdeg
alph_on=kon*(Kgli3*vff)/kdeg
beta_in=kin/kdeg
gmma_out=kout/kdeg
theta_c=kdegc/kdeg
alph_p=kcatp/(Kgli3*vff*kdeg)
beta_p=rbas/(Kgli3*vff*kdeg)
eps_out=kq/kdeg
dlta_in=kp/kdeg
ce=Kgli3/Kptc
; ******************************************************************************
;Define Nondimensional Shh binding equations
; Nondimensional variables:
;A = (mol Shh) / (L of extracellular liquid volume) / (Kgli3) / (vff)
;B = (mol membranic Ptc-Shh complex) / (L of extracellular liquid volume) / (Kgli3) / (vff)
;C = (mol intracellular Ptc-Shh complex) / (L of extracellular liquid volume) / (Kgli3)
;D = (mol membranic free Ptc) / (L of extracellular liquid volume) / (Kgli3) / (vff)
```

```
;E = (mol intracellular Ptc-Shh complex) / (L of intracellular liquid volume) / (Kgli3)
; Multimeric model from Lauffenberger 1993; Perelson 1986
;Bcom[i] = (mol membranic Ptc-Shh[i] complex) / (L of extracellular liquid volume) / (Kgli3) / (vff)
;Ccom[i] = (mol intracellular Ptc-Shh[i] complex) / (L of intracellular liquid volume) / (Kgli3)
; ********************************************************************************
d/dt (A) = 0
d/dt (D) = (alph_p)*Promoter + (beta_p)*Basal + (eps_out)*E − (alph_on)*A*D+k_x*Sum2−
kx*Sum1*D − (dlta_in)*D
d/dt (E) = (dlta_in)*D−(eps_out)*E−(theta_e)*E
sum1v[1..(f−1)]=(f−i)*Bcom[i]
sum1=arraysum(sum1v[*])
sum2v[1..f]=(i)*Bcom[i]
sum2=arraysum(sum2v[*])
f=5 ; maximum valency
INIT Bcom[1..f] = 0
d/dt (Bcom[1]) = (alph_on)*A*D − (alph_off)*Bcom[1] − (f−1)*kx*Bcom[1]*D +2*k_x*Bcom[2] −
(beta_in)*Bcom[1] + (gmma_out)*Ccom[1]
d/dt (Bcom[2..(f−1)]) = (f−i+1)*kx*Bcom[i−1]*D − i*k_x*Bcom[i] − (f−i)*kx*Bcom[i]*D +
(i+1)*k_x*Bcom[i+1] − (beta_in)*Bcom[i] + (gmma_out)*Ccom[i]
d/dt (Bcom[f]) = kx*Bcom[i−1]*D − f*k_x*Bcom[i] − (beta_in)*Bcom[i] + (gmma_out)*Ccom[i]
INIT Ccom[1..f] = 0
d/dt (Ccom[1..f]) = (beta_in)*Bcom[i] − (gmma_out)*Ccom[i] − (theta_c)*Ccom[i]
INIT A=Shh/(Kgli3*vff)
INIT D=Do/(Kgli3*vff)
INIT E=Eo/(Kgli3)
Signal=1/(1+ce*D) ; fraction of unbound Smo, based on Scatchard rxn between Ptc and Smo
kxfactor=12 ; acceleration of kon for multimeric Shh after initial binding
kx=alph_on*kxfactor
k_x=alph_off
; ********************************************************************************
;Define intracellular equations
; Nondimensional variables:
;G1 = (mol Gli1) / (L of intracellular liquid volume) / (Kgli3)
;G3 = (mol Gli3 activator form) / (L of intracellular liquid volume) / (Kgli3)
;G3R = (mol Gli3R repressor form) / (L of intracellular liquid volume) / (Kgli3)
; ********************************************************************************
d_G1=(alph)*Promoter + (beta)*Basal − G1
d/dt (G1) = (alph)*Promoter + (beta)*Basal − G1
d/dt (G3) = (gmma)/(G1+const) − G3*(1+(dlta)/(Kg3rc+Signal))
d/dt (G3R) = G3*(dlta)/(Kg3rc+Signal) − G3R
G3o=5.81e−9
G3Ro=61.2e−9
G1o=1.63e−9
INIT G1=G1o/Kgli3
INIT G3=G3o/Kgli3
INIT G3R=G3Ro/Kgli3
; -----------------------------------------------------------------------------------
;Define dimensional constants for intracellular equations
; -----------------------------------------------------------------------------------
basfactor=130
kcatg=1.992732e−10 ; maximum rate of Gli synthesis (2.4e−10 M/min)
rgbas=2.74e−10/basfactor ; Basal rate of Gli synthesis (vmax,g/100)
kcatp=1.5e−10; maximum rate of Ptc synthesis (4.5e−10 M/min)
rbas=2.25e−9/basfactor ; Basal rate of Ptc synthesis (vmax,P/100)
rg3b=3.1e−19 ; basal rate of gli3 synthesis (1.6e−19 M2/min)
Kshh=8.3e−10 ; Dissociation constant for Shh-Ptc binding
Kgli3=8.3e−10 ; used for Kptc
kdeg=0.009 ; Degradation rate constant for Gli 1 (.009 min−1)
kdegp=0.09 ; Degradation rate constant for Ptc (.045-0.071 min−1)
Kptc=3.32e−11 ; Half-maximal conc for Ptc which inhibits Smo signaling
kg3r=0.0117 ; rate constant for the conversion of Gli3 to Gli3R (0.012 min−1)
Kg3rc=0.12 ; Sensitivity constant of the conversion to signal strength
bc=1 ; binding cooperativity
tc=0.5 ; transcriptional efficiency
r=0.2 ; transcriptional repression
afr=0.5 ; affinity ratio
S=120
alph=kcatg/(Kgli3*kdeg)
beta=rgbas/(Kgli3*kdeg)
gmma=rg3b/(Kgli3*Kgli3*kdeg)
dlta=kg3r/kdeg
epsilon=kcatp/(kdeg*Kgli3)
etta=rbas/(Kgli3*kdeg)
const=1e−30
```

Results

Chemical Conjugation

Figures 2A, 2B:
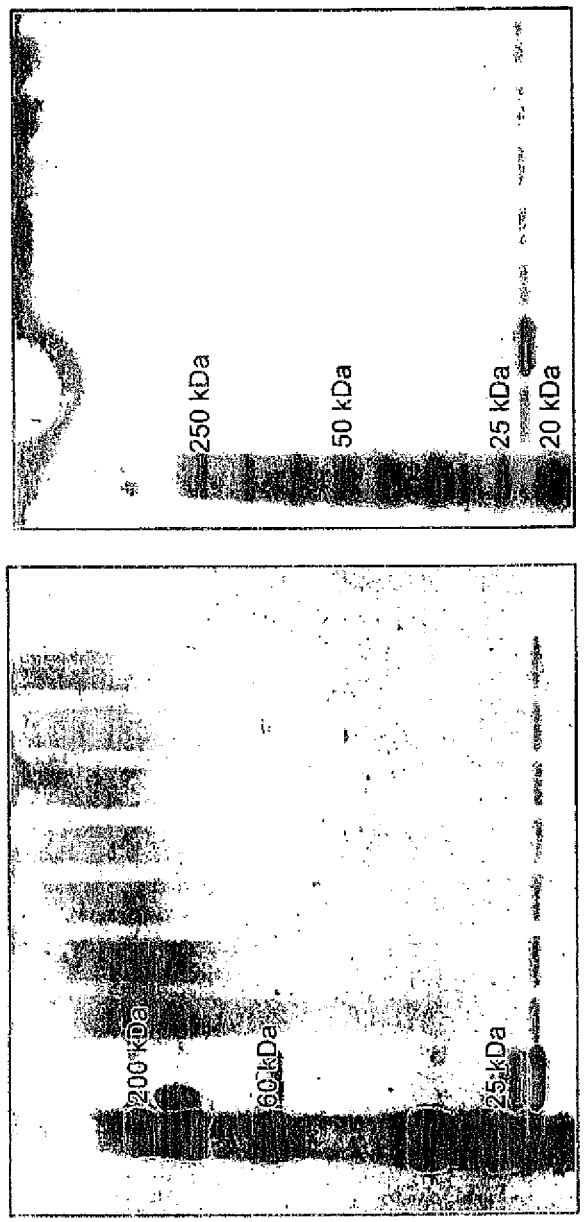
FIGS. 2A and 2B depict gel electrophoresis of Shh and its conjugation products with poly(acrylic acid) (pAAc) (FIG. 2A) and with HyA (FIG. 2B).

A recombinant rat Shh variant with a cysteine residue near the C-terminus was constructed, expressed, and purified via immobilized metal affinity chromatography. Conjugation of the recombinant protein was achieved on both pAAc and HyA with high efficiency. Using gel electrophoresis, it was apparent that the reaction produced a decrease in the monomeric Shh band (FIG. 2) and the appearance of a high molecular weight conjugate. For pAAc (FIG. 2A) (MW=450,000), this produced a smear through the gel with an increasing mass as the Shh conjugation molar feed ratio increased from 1:1 to 30:1. For HyA (MW=106 Da), the high molecular weight conjugates did not penetrate deeply into the gel (FIG. 2B). By contrast, simply mixing the Shh with raw pAAc or HyA did not alter the Shh mobility in the gel. Protein analysis of purified Shh:HyA reactions at 10:1 and 30:1 molar feed ratios performed in triplicate indicated that the reaction was reproducible with a high degree of efficiency at approximately 70-75% (Table 2). Molar feed ratios of 1:1, 5:1, 10:1, 20:1, and 30:1 produced Shh:HyA conjugates with molar substitution ratios of 0.6:1, 3.5:1, 7:1, 14:1, and 22:1, respectively.

TABLE 2

Determined conjugation ratios and coupling efficiencies for Shh:HyA reactions at 30:1 and 10:1 molar feed ratios.

| Feed Ratio | Molar Ratio of Shh:HyA | | Percent Coupling | |
|---|---|---|---|---|
|  | 30:1 | 10:1 | 30:1 | 10:1 |
| Trial 1 | 21.80 | 6.91 | 73.3% | 69.8% |
| Trial 2 | 22.58 | 6.65 | 76.0% | 67.1% |
| Trial 3 | 22.09 | 7.02 | 74.3% | 70.8% |
| Average | 22.16 | 6.86 | 74.5% | 69.2% |
| Stdev | 0.40 | 0.19 | 1.3% | 1.9% |

C3H10T1/2 Cell Bioactivity Assay

Through the use of the murine embryonic cell line C3H10T1/2, conjugation of the Shh was shown to dramatically alter the activity of the tethered protein when evaluated against actual Shh concentration in solution (FIG. 4). Only HyA-conjugated Shh could be tested using this cell line, as pAAc inhibited the differentiation that soluble Shh induces in the cell line. At low tethering (e.g., 3.5:1), the activity was decreased, with an estimated 10-fold increase in $EC_{50}$ of the Shh in solution, presumably due to steric hindrances that the large linear polymer caused when attached. The activity increased back to normal when the conjugation ratio reached 7:1. Beyond this, activity of the tethered Shh was increased dramatically, with a 10-fold decrease in estimated $EC_{50}$ values from the untethered Shh to the 22:1 construct.

CAM Angiogenesis Model

Figure 5:
FIGS. 5A-C present a panel of photomicrographs depicting chick chorioallantoic membrane (CAM) reactions to negative control samples (FIG. 5A), freely soluble Shh (FIG. 5B), and the 14:1 Shh/HyA multivalent form (FIG. 5C).
Figure 6:
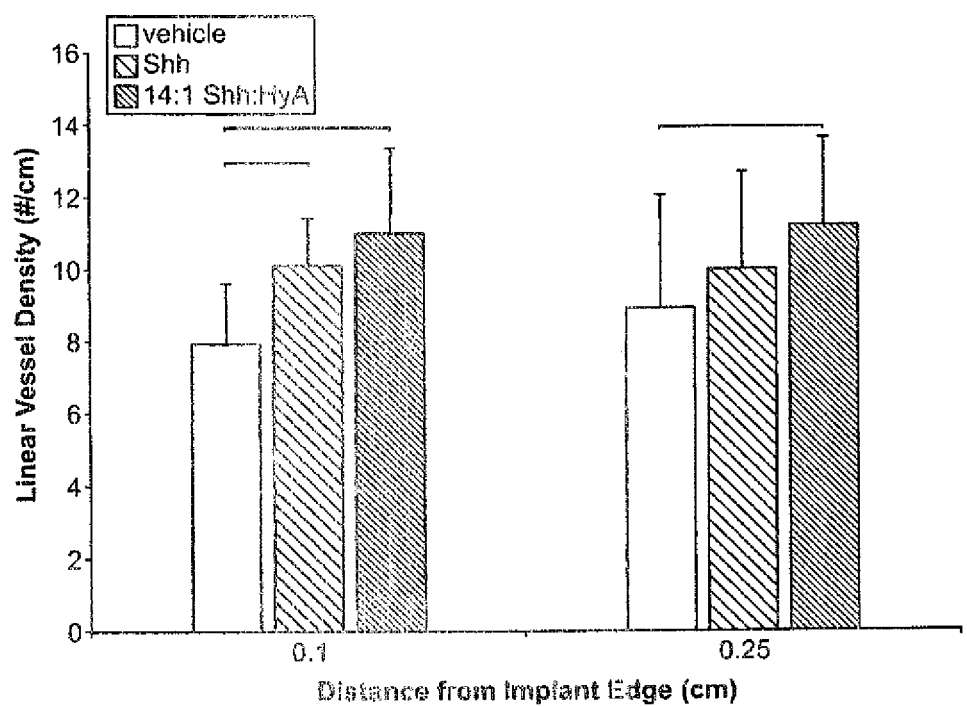
FIG. 6 depicts quantitative results of angiogenesis in the CAM assay derived from photomicrograph image analysis.

The CAM results indicated an increased potency for the conjugated Shh:HyA. Photographic analysis and quantification (FIGS. 5 and 6, respectively) revealed a statistically significant increase in vasculature around the Shh-loaded samples compared to the negative control within a close distance (0.1 mm) of the implant. While the Shh:HyA conjugated at a 14:1 ratio had an increased average vessel number over both the negative control and unconjugated Shh at 0.1 cm, it also had a longer-range persistent increase over the negative control at 0.25 cm. Although the soluble Shh also had an increased average vessel number over the negative control at this distance, this observation was not statistically significant.

Numerical Modeling of Multivalent Shh Bioactivity

Simple kinetic models of HyA:Shh conjugate binding, trafficking, and downstream signal activation was developed. To focus on the effects of conjugate multivalency, a number of assumptions were invoked in the simplified models: Ptc receptor aggregation does not affect signal transduction; ligand-internalization is not affected by valency; alkaline phosphatase activity is linearly proportional to Gli1 levels in a cell regardless of differentiation; and only two rates of conjugate binding occur—an initial binding of the conjugate and a higher binding rate for all additional Shh moieties from the conjugate to other Ptc receptors (see Methods section for model equations and Table 1 for parameters). With these assumptions, two types of models were developed, one incorporating steric hindrance of HyA chains as a simple reduction in conjugate binding affinity to Ptc, and one neglecting any influence of steric hindrance. These two models were termed "model with sterics" and "model without sterics," respectively. Under these assumptions, modeling results indicated that increasing the conjugation ratio of Shh to its HyA carrier in the bioactivity assay should result in a progressive increase in cell signaling and decrease in the $EC_{50}$ (FIG. 7). The estimated $EC_{50}$ values from the experimental data were well-matched using both types of kinetic models at the tested conjugation ratios and with the aforementioned assumptions ($R^2=0.7$ for the model without sterics; $R^2=0.8$ for the model with sterics). For the model without sterics, $EC_{50}$ values matched experimental results well at high conjugation ratios, but the modeling results over estimated the $EC_{50}$ values for conjugation ratios 7:1 and lower (FIG. 7). Results from the model with sterics can correct for this deviation (FIG. 7).

REFERENCES (1) Kuhl, P. R., and GriffithCima, L. G. (1996) Tethered epidermal growth factor as a paradigm for growth factor-induced stimulation from the solid phase. Nature Medicine 2, 1022-1027.

(2) Moon, J. J., Lee, S. H., and West, J. L. (2007) Synthetic biomimetic hydrogels incorporated with Ephrin-A1 for therapeutic angiogenesis. Biomacromolecules 8, 42-49.

(3) Seliktar, D., Zisch, A. H., Lutolf, M. P., Wrana, J. L., and Hubbell, J. A. (2004) MMP-2 sensitive, VEGF-bearing bioactive hydrogels for promotion of vascular healing. Journal of Biomedical Materials Research Part A 68A, 704-716.

(4) Zisch, A. H., Lutolf, M. P., Ehrbar, M., Raeber, G. P., Rizzi, S. C., Davies, N., Schmokel, H., Bezuidenhout, D., Djonov, V., Zilla, P., and Hubbell, J. A. (2003) Cell-demanded release of VEGF from synthetic, biointeractive cell-ingrowth matrices for vascularized tissue growth. Faseb Journal 17, 2260-+.

(5) Ooya, T., and Yui, N. (2002) Multivalent interactions between biotin-polyrotaxane conjugates and streptavidin as a model of new targeting for transporters. Journal of Controlled Release 80, 219-228.

(6) Segura, T., and Shea, L. D. (2002) Surface-tethered DNA complexes for enhanced gene delivery. Bioconjugate Chemistry 13, 621-629.

(7) Schaffer, D. V., and Lauffenburger, D. A. (1998) Optimization of cell surface binding enhances efficiency and specificity of molecular conjugate gene delivery. Journal of Biological Chemistry 273, 28004-28009.

(8) Thoma, G., Duthaler, R. O., Magnani, J. L., and Patton, J. T. (2001) Nanomolar E-selectin inhibitors: 700-fold potentiation of affinity by multivalent ligand presentation. Journal of the American Chemical Society 123, 10113-10114.
(9) Pouyani, T., and Prestwich, G. D. (1994) Functionalized Derivatives of Hyaluronic-Acid Oligosaccharides—Drug Carriers and Novel Biomaterials. Bioconjugate Chemistry 5, 339-347.
(10) York, S. J., Arneson, L. S., Gregory, W. T., Dahms, N. M., and Kornfeld, S. (1999) The rate of internalization of the mannose 6-phosphate/insulin-like growth factor II receptor is enhanced by multivalent ligand binding. Journal of Biological Chemistry 274, 1164-1171.
(11) Hlavacek, W. S., Posner, R. G., and Perelson, A. S. (1999) Steric effects on multivalent ligand-receptor binding: Exclusion of ligand sites by bound cell surface receptors. Biophysical Journal 76, 3031-3043.
(12) Hubble, J. (1999) A model of multivalent ligand-receptor equilibria which explains the effect of multivalent binding inhibitors. Molecular Immunology 36, 13-18.
(13) Muller, K. M., Arndt, K. M., and Pluckthun, A. (1998) Model and simulation of multivalent binding to fixed ligands. Analytical Biochemistry 261, 149-158.
(14) Huskens, J., Mulder, A., Auletta, T., Nijhuis, C. A., Ludden, M. J. W., and Reinhoudt, D. N. (2004) A model for describing the thermodynamics of multivalent host-guest interactions at interfaces. Journal of the American Chemical Society 126, 6784-6797.
(15) Lai, K., Kaspar, B. K., Gage, F. H., and Schaffer, D. V. (2003) Sonic hedgehog regulates adult neural progenitor proliferation in vitro and in vivo. Nature Neuroscience 6, 21-27.
(16) Pepinsky, R. B., Rayhorn, P., Day, E. S., Dergay, A., Williams, K. P., Galdes, A., Taylor, F. R., Boriack-Sjodin, P. A., and Garber, E. A. (2000) Mapping Sonic hedgehog-receptor interactions by steric interference. Journal of Biological Chemistry 275, 10995-11001.
(17) Stile, R. A., and Healy, K. E. (2001) Thermo-responsive peptide-modified hydrogels for tissue regeneration. Biomacromolecules 2, 185-194.
(18) Taylor, F. R., Wen, D. Y., Garber, E. A., Carmillo, A. N., Baker, D. P., Arduini, R. M., Williams, K. P., Weinreb, P. H., Rayhorn, P., Hronowski, X. P., Whitty, A., Day, E. S., Boriack-Sjodin, A., Shapiro, R. I., Galdes, A., and Pepinsky, R. B. (2001) Enhanced potency of human sonic hedgehog by hydrophobic modification. Biochemistry 40, 4359-4371.
(19) Pepinsky, R. B., Zeng, C. H., Wen, D. Y., Rayhorn, P., Baker, D. P., Williams, K. P., Bixler, S. A., Ambrose, C. M., Garber, E. A., Miatkowski, K., Taylor, F. R., Wang, E. A., and Galdes, A. (1998) Identification of a palmitic acid-modified form of human Sonic hedgehog. Journal of Biological Chemistry 273, 14037-14045.
(20) Pola, R., Ling, L. E., Silver, M., Corbley, M. J., Kearney, M., Pepinsky, R. B., Shapiro, R., Taylor, F. R., Baker, D. P., Asahara, T., and Isner, J. M. (2001) The morphogen Sonic hedgehog is an indirect angiogenic agent upregulating two families of angiogenic growth factors. Nature Medicine 7, 706-711.
(21) Saha, K., and Schaffer, D. V. (2006) Signal dynamics in Sonic hedgehog tissue patterning. Development 133, 889-900.
(22) Lai, K., Robertson, M. J., and Schaffer, D. V. (2004) The Sonic hedgehog signaling system as a bistable genetic switch. Biophysical Journal 86, 2748-2757.
(23) Perelson, A. S. (1981) Receptor Clustering on a Cell-Surface 0.3. Theory of Receptor Cross-Linking by Multivalent Ligands—Description by Ligand States. Mathematical Biosciences 53, 1-39.
(24) Lauffenburger, D. A., and Linderman, J. J. (1993) Receptors: Models for Binding, Trafficking, and Signaling.
(25) Vercruysse, K. P., Marecak, D. M., Marecek, J. F., and Prestwich, G. D. (1997) Synthesis and in vitro degradation of new polyvalent hydrazide cross-linked hydrogels of hyaluronic acid. Bioconjugate Chemistry 8, 686-694.
(26) Bulpitt, P., and Aeschlimann, D. (1999) New strategy for chemical modification of hyaluronic acid: Preparation of functionalized derivatives and their use in the formation of novel biocompatible hydrogels. Journal of Biomedical Materials Research 47, 152-169.
(27) Stile, R. A., Barber, T. A., Castner, D. G., and Healy, K. E. (2002) Sequential robust design methodology and X-ray photoelectron spectroscopy to analyze the grafting of hyaluronic acid to glass substrates. Journal of Biomedical Materials Research 61, 391-398.
(28) Shu, X. Z., Liu, Y. C., Luo, Y., Roberts, M. C., and Prestwich, G. D. (2002) Disulfide cross-linked hyaluronan hydrogels. Biomacromolecules 3, 1304-1311.
(29) Luo, Y., Ziebell, M. R., and Prestwich, G. D. (2000) A hyaluronic acid-taxol antitumor bioconjugate targeted to cancer cells. Biomacromolecules 1, 208-218.
(30) Luo, Y., and Prestwich, G. D. (1999) Synthesis and selective cytotoxicity of a hyaluronic acid-antitumor bioconjugate. Bioconjugate Chemistry 10, 755-763.
(31) Feng, J., White, B., Tyurina, O. V., Guner, B., Larson, T., Lee, H. Y., Karlstrom, R. O., and Kohtz, J. D. (2004) Synergistic and antagonistic roles of the Sonic hedgehog N- and C-terminal lipids. Development 131, 4357-4370.
(32) Torroja, C., Gorfinkiel, N., and Guerrero, I. (2004) Patched controls the Hedgehog gradient by endocytosis in a dynamin-dependent manner, but this internalization does not play a major role in signal transduction. Development 131, 2395-2408.
(33) Incardona, J. P., Lee, J. H., Robertson, C. P., Enga, K., Kapur, R. P., and Roelink, H. (2000) Receptor-mediated endocytosis of soluble and membrane-tethered Sonic hedgehog by Patched-1. Proceedings of the National Academy of Sciences of the United States of America 97, 12044-12049.
(34) Stile, R. A., Chung, E., Burghardt, W. R., and Healy, K. E. (2004) Poly(N-isopropylacrylamide)-based semi-interpenetrating polymer networks for tissue engineering applications. Effects of linear poly(acrylic acid) chains on rheology. Journal of Biomaterials Science-Polymer Edition 15, 865-878.
(35) Chung, E. H., Gilbert, M., Virdi, A. S., Sena, K., Sumner, D. R., and Healy, K. E. (2006) Biomimetic artificial ECMs stimulate bone regeneration. Journal of Biomedical Materials Research Part A 79A, 815-826.
Chen, C.-H., D. P. v. Kessler, et al. (1999). "Nuclear Trafficking of Cubitus interruptus in the Transcriptional Regulation of Hedgehog Target Gene Expression." Cell 98: 305-316.
French, A. R. and D. A. Lauffenburger (1996). "Intracellular receptor/ligand sorting based on endosomal retention components." Biotechnology and Bioengineering 51(3): 281-297.
Fuse, N., T. Maiti, et al. (1999). "Sonic hedgehog protein signals not as a hydrolytic enzyme but as an apparent ligand for patched." Proc Natl Acad Sci USA 96(20): 10992-9.

Keller, A. D. (1995). "Model genetic circuits encoding autoregulatory transcription factors." Journal of Theoretical Biology 172(2): 169-185.

Lai, K., M. J. Robertson, et al. (2004). "The Sonic Hedgehog Signaling System as a Bistable Genetic Switch." Biophysical Journal 86: 2748-2757.

Lander, A. D., Q. Nie, et al. (2002). "Do morphogen gradients arise by diffusion?" Dev Cell 2(6): 785-96.

Lauffenburger, D. A. and J. J. Linderman (1993). Receptors: Models for binding, trafficking, and signaling. New York, Oxford University Press.

Taipale, J., M. K. Cooper, et al. (2002). "Patched acts catalytically to suppress the activity of Smoothened." Nature 418: 892-7.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A conjugate of the formula:

$$[X-(Y)_n]_{10-50}-Z,$$

where X is a biologically active polypeptide having a molecular weight of from about 5 kDa to about 50 kDa;

Y is an optional linker moiety, wherein n is 0 or an integer from 1 to about 10; and Z is a biocompatible polymer having a molecular weight of at least about 50,000 Daltons, and wherein the polypeptide is covalently linked to the polymer directly or via the linker moiety.

2. The conjugate of claim 1, wherein the polymer is a linear polymer comprising multiple subunits selected from hyaluronic acid, acrylic acid, ethylene glycol, methacrylic acid, acrylamide, hydroxyethyl methacrylate, mannitol, maltose, glucose, arabinose, taurine, betaine, modified celluloses, hydroxyethyl cellulose, ethyl cellulose, methyl cellulose, hydroxyethyl methyl cellulose, hydroxypropyl methyl cellulose, carboxymethyl cellulose, modified starches, hydrophobically modified starch, hydroxyethyl starch, hydroxypropyl starch, amylose, amylopectin, oxidized starch, and copolymers thereof.

3. The conjugate of claim 1, wherein the biologically active polypeptide is a receptor, a ligand for a receptor, a growth factor, an angiogenic factor, a polypeptide that induces cell differentiation, an antibody, or a polypeptide that inhibits cell proliferation.

4. The conjugate of claim 1, wherein the polymer is linear poly(acrylic acid).

5. The conjugate of claim 1, wherein the polymer is hyaluronic acid.

6. A pharmaceutical composition comprising:
a) the conjugate of claim 1; and
b) a pharmaceutically acceptable excipient.

7. An implantable device comprising the conjugate of claim 1.

8. The implantable device of claim 7, wherein the implantable device is a stent, a shunt, an artificial valve, a lead, an artificial joint, a graft, or an electrode.

9. An implantable drug delivery device comprising the conjugate of claim 1.

* * * * *